United States Patent
Fukui et al.

(10) Patent No.: US 7,541,153 B2
(45) Date of Patent: Jun. 2, 2009

(54) METHOD OF SCREENING A SUBSTANCE INTERFERING IN THE ASSOCIATION OF DOCK2 AND ELMO

(75) Inventors: Yoshinori Fukui, Fukuoka (JP); Takehiko Sasazuki, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 325 days.

(21) Appl. No.: 10/535,223

(22) PCT Filed: Nov. 14, 2003

(86) PCT No.: PCT/JP03/14538

§ 371 (c)(1),
(2), (4) Date: Mar. 27, 2006

(87) PCT Pub. No.: WO2004/048974

PCT Pub. Date: Jun. 10, 2004

(65) Prior Publication Data

US 2006/0234294 A1    Oct. 19, 2006

(30) Foreign Application Priority Data

Nov. 26, 2002   (JP) ............................. 2002-342683

(51) Int. Cl.
*G01N 33/53* (2006.01)
(52) U.S. Cl. ...................................................... 435/7.1
(58) Field of Classification Search .................... None
See application file for complete search history.

(56) References Cited

U.S. PATENT DOCUMENTS 4,996,193 A * 2/1991 Hewitt et al. ................... 514/11

OTHER PUBLICATIONS

Patent Abstracts of Japan—English language machine translation of JP 2002-342683, published as 2004-177226A, Claims (2004).*
Patent Abstracts of Japan—English language machine translation of JP 2002-342683, published as 2004-177226A, Description (2004).*
Agrawal, Vishal et al., "Promiscuous Binding Nature of SH3 Domains to Their Target Proteins", Protein and Peptide Letters, vol. 9, No. 3, 2002, pp. 185-193.

(Continued)

*Primary Examiner*—Cherie M Woodward
(74) *Attorney, Agent, or Firm*—Foley & Lardner LLP

(57) ABSTRACT

The present invention is related to provide a method for screening a substance interfering in the association of DOCK2 and ELMO1, a method for screening a substance interfering in the association of ELMO1 and Tiam1, and a method for searching a therapeutic agent for immune related diseases such as allergy, autoimmune diseases, GvH, graft rejection with the use of these searching methods, and so on. It was found that in DOCK2-mutant lacking 504 amino acid residues at the N terminus of DOCK2, Rac-activating ability was significantly decreased, and that actin polymerization could not be induced, and ELMO1 was identified as a molecule binding to this domain. It was found that DOCK2 was associated to ELMO1 via SH3 domain. Moreover, it was found that ELMO1 is bound with Tiam1 functioning as Rac-specific GDP/GTP exchange factor (GEF). It was found that DOCK2 activates Rac by recruiting Tiam1 via ELMO1.

7 Claims, 6 Drawing Sheets

OTHER PUBLICATIONS

Brugnera, Enrico et al., "Unconventional Rac-GEF Activity is Mediated Through the DOCK180-ELMO Complex", Nature Cell Biology, vol. 4, Aug. 2002, pp. 574-583.

Li, Shaun S.-C., "Specificity and Versatility of SH3 and Other Proline-Recognition Domains: Structural Basis and Implications for Cellular Signal Transduction", Biochem J., vol. 390, 2005, pp. 641-653.

Nishihara, Hiroshi et al, "DOCK2 Associates with CrkL and Regulates Rac 1 in Human Leukemia Cell Lines", Blood, vol. 100, No. 12, Dec. 1, 2002, pp. 3968-3974.

Fukui, Yoshinori et al., "Haematopoietic cell-specific CDM family protein DOCK2 is essential for lymphocyte migration", *Nature*, vol. 412, (2001), pp. 826-831.

Gumienny, Tina et al., "CED-12/ELMO, a Novel Member of the Crkll/Dock180/Rac Pathway, Is Required for Phagocytosis and Cell Migration", *Cell*, vol. 107, (2001), pp. 27-41.

Michiels, Frits et al., "A role for Rac in Tiam1-induced membrane ruffling and invasion", *Letters to Nature*, vol. 375, (1995), pp. 338-340.

Nishihara, Hiroshi et al., "DOCK2 mediates T cell receptor-induced activation of Rac2 and IL-2 transcription", *Biochemical and Biophysical Research Communications*, vol. 296, (2002), pp. 716-720.

Nishihara, Hiroshi et al., "Non-adherent cell-specific expression of DOCK2, a member of the human CDM-family proteins", *Biochimica et Biophysica Acta*, vol. 1452, (1999), pp. 179-187.

Reif, Karin et al., "The CDM protein DOCK2 in lymphocyte migration", Trends in Cell Biology, vol. 12, No. 8, Aug. 2002, pp. 368-373.

Sanui T. et al., "DOCK2 regulates Rac activation and cytoskeletal reorganization through interaction with ELMO1", Blood, vol. 102, No. 8, Oct. 2003, pp. 2948-2950.

\* cited by examiner

METHOD OF SCREENING A SUBSTANCE INTERFERING IN THE ASSOCIATION OF DOCK2 AND ELMO

TECHNICAL FIELD

The present invention relates to the identification of DOCK2 domain by using a deletion mutant, and a method for screening a substance interfering in the binding of DOCK 2 and SH3 domain of DOCK 2, particularly to a method for screening a substance interfering in the association of DOCK2 and ELMO, a method for screening a substance interfering in the association of ELMO and GDP/GTP exchange factor such as Tiam, or to a method for searching therapeutic agents for immune-related diseases, such as allergy, autoimmune diseases, GvH or graft rejection, with the use of these screening methods.

BACKGROUND ART

Immune response is a regulatory mechanism indispensable against infection for a living body, and immune cells are patrolling constantly in the living body, to respond rapidly to various sources of infection. Such characteristics that constitutive cells are moving continuously are not recognized in other complex living systems, and have been developed specifically in the immune system. Among the immune cells, cells such as neutrophils, macrophages are known to function during primary defense of infection, while T- and B-lymphocytes trigger antigen-specific immune response by recognizing external foreign substances via the antigen receptor. The above T- and B-lymphocytes differentiate in primary lymphoid organs such as thymus and bone marrow, and transfer to a particular compartment in second lymphoid organs such as spleen, lymph nodes, Payer's patch (lymphoid organs in the small intestine), and by recognizing antigens gathered there from various organs via the antigen receptor, induce specific immune response. At that time, the transfer of lymphocytes to a particular site of second lymphoid organ is very important for the formation of immune response. Heretofore, the transfer of the lymphocytes was known to be induced by protein called generally various chemokines, while the molecule mechanism that controls the mobility of the lymphocytes themselves remained unknown.

Change of cell polarization and cytoskeletal reorganization were indispensable for the cells movement (Cell 84, 359-369, 1996), and these were known to be controlled by G protein of low molecular weight such as Rho, Rac and Cdc42 (Proc. Natl. Acad. Sci. USA 92, 5027-5031, 1995; Science 279, 509-514, 1998; J. Cell Biol. 141, 1147-1157, 1998; Science 287, 1037-1040, 2000). Among these, Rac particularly provides driving force at the time of cell migration, by forming an actin-rich protrusion, called foliar protrusion (Science 279, 509-514, 1998; Cell 103, 227-238, 2000). On the other hand, molecules showing structural homology called CED5, DOCK 180 and Myoblast city (MBC) were identified in *Caenorhabditis elegans*, human and *Drosophila melanogaster*. These molecules are called CDM family molecules by their initials, and all of them are thought to be related to cytoskeletal reorganization by functioning upstream of Rac (Cell 84, 359-369, 1996; J. Cell Biol. 138, 589-603, 1997; Nature 392, 501-504, 1998; Genes Dev. 12, 3331-3336, 1998; Genes Dev. 12, 3337-3342, 1998; Nature Cell Biol. 2, 131-136, 2000). Although genetic analysis with the use of a deletion mutant has shown that the above CED-5 and Myoblast City are crucial for cell migration of particular types of cells, (J. Cell Biol. 138, 589-603, 1997; Nature 392, 501-504, 1998; Nature Cell Biol. 2, 131-136, 2000), physiological relevance of the CDM family proteins in mammals remained unknown.

It is known that DOCK2 (KIAA0209; DNA Res. 3, 321-329) encodes another member of the CDM family proteins, which is specifically expressed in human haematopoietic cells, and that the DOCK2 binds to activate Rac in 293T kidney cells (Biochem. Biophys. Acta 1452, 179-187, 1999). On the other hand, the present inventors isolated a new gene Hch belonging to the CDM family from mouse thymus cDNA library, and found that the gene product comprises 1828 amino acids, and encodes SH3 domain at the N terminus (Nature, 412, 826-831, 2001). Moreover, the present inventors confirmed by Northen Blot analysis using mouse organs that whereas DOCK180 was expressed in various organs, the expression of Hch was restricted to thymus and spleen. Further, by an analysis using cell lines they confirmed that Hch expression was observerd in all T-, B- and macrophage cells, with the exception of two mutant T-cell lines. Furthermore, it has been revealed that a significant change in cell morphology and enhancement of adhesion were observed by introducing Hch into mutant T-cell line lacking Hch expression. Though 1677 of the 1828 amino acids encoded by Hch are identical to human DOCK2, and Hch was thought to be mouse DOCK2 homologue, the physiological function remained unknown.

The present inventors identified DOCK2 as a molecule belonging to the CDM family, expressing specifically in lymphocytes as mentioned above, and by generating the knockout mice, they revealed that the molecule was indispensable to lymphocyte migration (Nature, 412, 826-831, 2001). In DOCK2-deleted lymphocytes, active Rac is not detected by any of chemokine stimulation. Therefore, it can be thought that DOCK2 regulates lymphocyte migration via Rac activation. However, it remains unknown by which mechanism DOCK2 activates Rac. Rac functions as a molecule switch, and is activated by a GDP/GTP exchange factor (GEF). Though DOCK2 binds with Rac, it is hard from its structure, to think that it functions as GEF. Therefore, it is estimated that DOCK2 activates Rac by recruiting GEF via other molecules.

Recently, CED-12 being a molecule that associates with CED-5, which is one of the CDM family molecules, and that regulates cytoskeleton has been identified in *C. elegans*, and ELMO-1, -2 and -3 were reported as their mammalian homologues (Cell, 107, 27-41, 2001). Moreover, several dozens of GDP/GTP exchange factors (GEF) were known heretofore, and among these GEFs, as a molecule functioning as Rac-specific GEF, the following are known: Tiam-1 and -2 that determines the invasion to thymoma cell lines (Cell, 77, 537-549, 1994; Nature, 375, 338-340, 1995); Vav1 that regulates T cell receptor signal (Nature, 385, 169-172, 1997) besides Vav2, Vav3; Trio (J. Cell Science, 113, 729-739, 2000); STEF (J. Biol. Chem., 277, 2860-2868, 2002); and P-Rex1 (Cell, 108, 809-821, 2002). All these five molecules have a common domain, and comprise a function to provide GTP to Rac.

Autoimmune diseases and graft rejection are caused by the invasion of lymphocytes into the target organ. Therefore, it is thought that DOCK2 might be a suitable target molecule to treat or prevent such diseases or pathology. The object of the present invention is to identify the functional domain of DOCK2 by using a deletion mutant, to screen a substance interfering in the binding of DOCK2 and SH3 domain of DOCK2, particularly to provide a method for screening a substance interfering in the association of DOCK2 and ELMO, a method for screening a substance interfering in the association of ELMO and GDP/GTP exchange factor such as Tiam, or a method for searching therapeutic agents for immune-related diseases, such as allergy, autoimmune diseases, GvH or graft rejection with the use of these screening methods, and the like.

DOCK2 is a molecule expressed specifically in lymphocytes, comprised of 1828 amino acid residues including SH3 domain, that activates Rac and regulates cytoskeleton to determine lymphocyte mobility. The present inventors have made a keen study to solve the above object, found that Rac-activating ability was significantly decreased in DOCK2 mutant lacking 504 amino acid residues in the N terminus including SH3 domain of DOCK 2, and that actin polymerization could not be induced, and they identified ELMO1 as a molecule binding to this domain. Moreover, as the binding of DOCK2 and ELMO1 was completely inhibited by the single amino acid mutation of SH3 domain, they have found that DOCK2 associates with ELMO1 via SH3 domain. Furthermore, they have found that ELMO1 binds with Tiam1 functioning as Rac-specific GDP/GTP exchange factor (GEF). In other words, they have found that DOCK2 activates Rac by recruiting Tiam1 via ELMO1. Therefore, they found that by inhibiting intermolecular interaction of SH3 domain of DOCK2, ELMO1 and Tiam1, the artificial control of lymphocyte migration was possible. The present invention has been thus completed with this knowledge.

DISCLOSURE OF THE INVENTION

In other words, the present invention relates to a method for screening a substance interfering in the association of DOCK2 and ELMO, comprising the steps of contacting DOCK2, ELMO and a test substance, and then estimating the level of formation of association of DOCK2 and ELMO ("1"); a method for screening a substance interfering in the association of DOCK2 and ELMO, comprising the steps of contacting SH3 domain of DOCK2, ELMO and a test substance, and then estimating the level of formation of association of SH3 domain of DOCK2 and ELMO ("2"); a method for screening a substance interfering in the association of DOCK2 and C terminus domain of ELMO, comprising the steps of contacting DOCK2, C terminus domain of ELMO and a test substance, and then estimating the level of formation of association of DOCK2 and C terminus domain of ELMO("3"); a method for screening a substance interfering in the association of DOCK2 and ELMO, comprising the steps of contacting SH3 domain of DOCK2, C terminus domain of ELMO and a test substance, and then estimating the level of formation of association of SH3 domain of DOCK2 and C terminus domain of ELMO ("4"); the method for screening a substance interfering in the association of DOCK2 and ELMO according to any one of "1" to "4", wherein DOCK2 or its SH3 domain and/or ELMO or its C-terminus domain is bound with a marker protein and/or peptide tag ("5"); the method for screening a substance interfering in the association of DOCK2 and ELMO according to anyone of "1" to "5", wherein an antibody against ELMO or its C terminus domain is acted to DOCK2 or its SH3 domain fractionated by an antibody against DOCK2 or its SH3 domain, or an antibody against other peptides fused with DOCK2 or its SH3 domain, and the level of formation of association is estimated ("6"); the method for screening a substance interfering in the association of DOCK2 and ELMO according to any one of "1" to "6", wherein the level of formation of association is estimated by detecting GTP-binding form of activated-Rac ("7"); the method for screening a substance interfering in the association of DOCK2 and ELMO according to any one of "1" to "7", wherein the substance interfering in the association of DOCK2 and ELMO is a substance promoting or suppressing the function of regulating lymphocyte migration ("8"); the method for screening a substance interfering in the association of DOCK2 and ELMO according to any one of "1" to "7", wherein the substance interfering in the association of DOCK2 and ELMO is a substance inhibiting the binding of DOCK2 and ELMO ("9"); the method for screening a substance interfering in the association of DOCK2 and ELMO according to any one of "1" to "9", wherein ELMO is ELMO1 ("10"); a method for searching a therapeutic agent for immune related diseases such as allergy, autoimmune diseases, GvH, and graft rejection wherein the method for screening a substance interfering in the association of DOCK2 and ELMO according to any one of "1" to "10" is used ("11"); and a method for searching a therapeutic agent for diseases caused by the suppression of lymphocyte migration, which promotes cytoskeletal reorganization by activating Rac, wherein the method for screening a substance interfering in the association of DOCK2 and ELMO according to any one of "1" to "10" is used ("12").

Moreover, the present invention is related to a method for screening a substance interfering in the association of ELMO and GDP/GTP exchange factor, comprising the steps of contacting ELMO, GDP/GTP exchange factor and a test substance, and then estimating the level of formation of association of ELMO and GDP/GTP exchange factor ("13"); a method for screening a substance interfering in the association of ELMO and GDP/GTP exchange factor, comprising the steps of contacting N terminus domain of ELMO, GDP/GTP exchange factor and a test substance, and then estimating the level of formation of association of N terminus domain of ELMO and GDP/GTP exchange factor ("14"); the method for screening a substance interfering in the association of ELMO and GDP/GTP exchange factor according to "13" or "14", wherein ELMO or its N terminus domain and/or GDP/GTP exchange factor is fused with another peptide ("15"); the method for screening a substance interfering in the association of ELMO and GDP/GTP exchange factor according to any one of "13" to "15", wherein an antibody against ELMO or its N terminus domain is acted to a GDP/GTP exchange factor fractionated by an antibody against GDP/GTP exchange factor or by an antibody against another peptide fused with GDP/GTP exchange factor, and the level of formation of association is estimated ("16"); the method for screening a substance interfering in the association of ELMO and GDP/GTP exchange factor according to any one of "13" to "16", wherein the level of formation of association is estimated by detecting GTP-binding form of activated-Rac ("17"); the method for screening a substance interfering in the association of ELMO and GDP/GTP exchange factor according to any one of "13" to "17", wherein the substance interfering in the association of ELMO and GDP/GTP exchange factor is a substance promoting or suppressing the function of regulating lymphocyte migration ("18"); the method for screening a substance interfering in the association of ELMO and GDP/GTP exchange factor according to any one of "13" to "17", wherein the substance interfering in the association of ELMO and GDP/GTP exchange factor is a substance inhibiting the binding of ELMO and GDP/GTP exchange factor ("19"); the method for screening a substance interfering in the association of ELMO and GDP/GTP exchange factor according to any one of "13" to "19", wherein ELMO is an ELMO bound with DOCK2 ("20"); the method for screening a substance interfering in the association of ELMO and GDP/GTP exchange factor according to any one of "13" to "20", wherein ELMO is ELMO1 ("21"); the method for screening a substance interfering in the association of ELMO and GDP/GTP exchange factor according to any one of "13" to "21", wherein the GDP/GTP exchange factor is a Rac-specific GDP/GTP exchange factor ("22"); the method for screening a substance interfering in the association of ELMO and GDP/GTP exchange factor according to "22", wherein the Rac-specific GDP/GTP exchange factor is Tiam1 ("23"); a method for searching a therapeutic agent for immune related diseases such as allergy, autoimmune diseases, GvH, and graft rejection, wherein the method for screening a substance interfering in the association of ELMO and GDP/GTP exchange factor according to any one of "13" to "23" is used ("24"); and a method for searching a therapeutic agent for diseases caused by the suppression of lymphocyte migration, which promotes cytoskeletal reorganization by activating Rac, wherein the method for screening a substance interfering in the association of ELMO and GDP/GTP exchange factor according to any one of "13" to "23" is used ("25").

Furthermore, the present invention relates to a method for screening a substance for promoting or suppressing Rac activation, comprising the steps of contacting DOCK2, ELMO, GDP/GTP exchange factor and a test substance, and then estimating the level of formation of association of DOCK2 and ELMO, or the level of formation of association of ELMO and GDP/GTP exchange factor ("26"); a method for screening a substance for promoting or suppressing Rac activation, comprising the steps of contacting SH3 domain of DOCK2, ELMO, GDP/GTP exchange factor and a test substance and then estimating the level of formation of association of SH3 domain of DOCK2 and ELMO, or the level of formation of association of ELMO and GDP/GTP exchange factor ("27"); the method for screening a substance for promoting or suppressing Rac activation according to "26" or "27", wherein the level of formation of association is estimated by detecting GTP-binding form of activated-Rac ("28"); the method for screening a substance for promoting or suppressing Rac activation according to any one of "26" to "28", wherein ELMO is an ELMO bound with DOCK2 ("29"); the method for screening a substance for promoting or suppressing Rac activation according to any one of "26" to "29", wherein ELMO is ELMO1 ("30"); the method for screening a substance for promoting or suppressing Rac activation according to any one of "26" to "30", wherein the GDP/GTP exchange factor is a Rac-specific GDP/GTP exchange factor ("31"); the method for screening a substance for promoting or suppressing Rac activation according to "31", wherein the Rac-specific GDP/GTP exchange factor is Tiam1 ("32"); a method for searching a substance for promoting or suppressing the function of regulating lymphocyte migration, wherein the method for screening a substance promoting or suppressing Rac activation according to any one of "26" to "32" is used ("33"); a method for searching a therapeutic agent for immune related diseases such as allergy, autoimmune diseases, GvH, and graft rejection, wherein the method for screening a substance for promoting or suppressing Rac activation according to any one of "26" to "32" is used ("34"); and a method for searching a therapeutic agent for diseases caused by the suppression of lymphocyte migration, which promotes reconstruction of cytoskeleton by activating Rac, wherein the method for screening a substance for promoting or suppressing Rac activation according to any one of "26" to "32" is used ("35"); a therapeutic agent for immune related diseases such as allergy, autoimmune diseases, GvH and graft rejection, obtained by the searching method according to "11", "24" or "34" ("36"); a therapeutic agent for diseases caused by the suppression of lymphocyte migration, promoting cytoskeletal reorganization by activating Rac, obtained by the searching method according to "12", "25" or "35" ("37"); a method for screening a substance inhibiting DOCK2-function, by targeting N terminus domain of DOCK2 including SH3 domain, comprising the steps of contacting SH3 domain of DOCK2, the SH3 domain-binding protein and a test substance, and then estimating the level of formation of association of DOCK2 and SH3 domain-binding protein ("38"); and a method for screening a substance inhibiting DOCK2-function, by using a transgenic cell line expressing full-length DOCK2 and DOCK2-deleted mutants, comprising the steps of measuring and estimating the level of Rac activation in these cell lines, identifying the functional domain of DOCK2, searching a molecule associated with functional domain that associates with the functional domain, contacting the functional domain of DOCK2, the molecule associated with functional domain and a test substance, and estimating the level of formation of association of functional domain of DOCK2 and molecule associated with functional domain of DOCK2 ("39").

A is a view showing a frame format of the structure of DOCK2 and DOCK2-deleted mutants. In the figure, the black-colored part is the SH3 domain.

B is a figure showing the analysis of the binding with ELMO1 by immunoprecipitation and Western Blot method, by transfecting genes encoding DOCK2 or DOCK2-deleted mutants to 293T cells with PcDNA ELMO1-V5 and by collecting the cells 48 hours later. Types of samples used for analysis, antibodies used for immunoprecipitation and Western Blot are shown on the left side.

Figure 2:
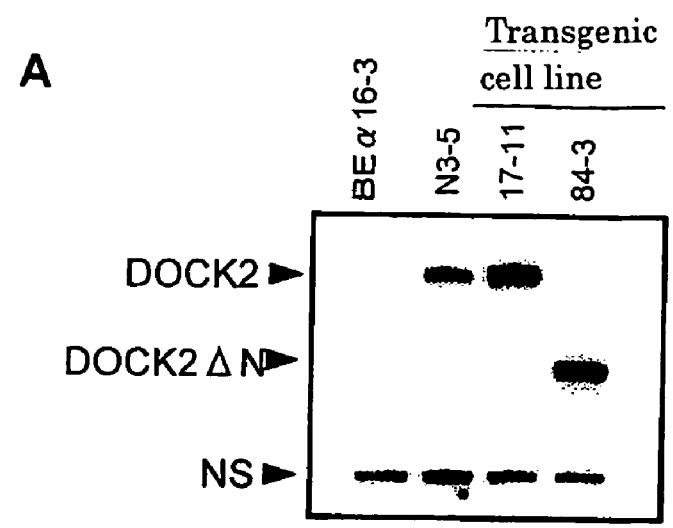
Figure 2:
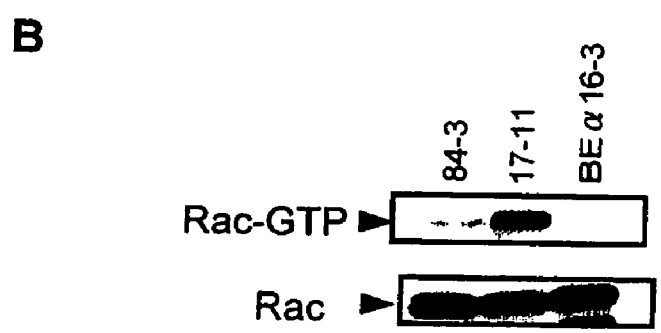
Figure 2:
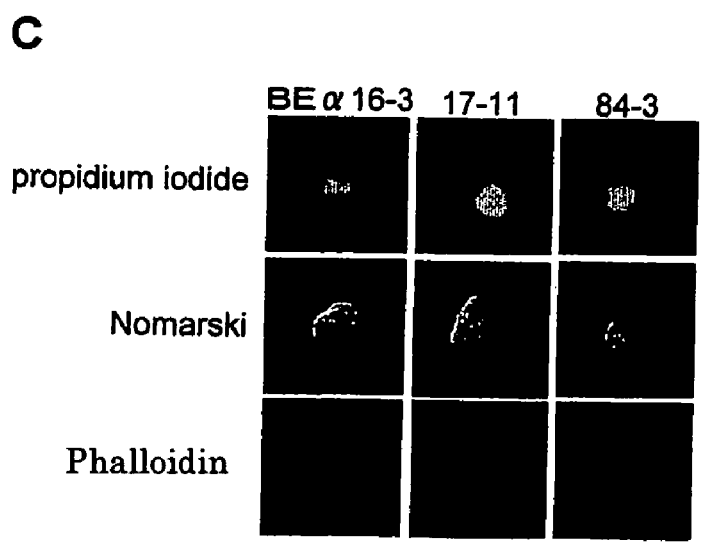

FIG. 2 is a set of pictures showing that the Rac-activating ability is significantly decreased and that actin polymerization cannot be induced in DOCK2ΔN lacking N terminus domain essential for the binding with ELMO1.

A is a picture showing the analysis of the expression of DOCK2 or DOCK2ΔN in BEα16-3, N3-5, and transgenic cell lines (17-11, 84-3) by Western Blot with the use of polyclonal antibody against DOCK2. In the figures, NS means non-specific band.

B is a picture that activated Rac is detected by pulling-down cell extract of 84-3, 17-11, BEα16-3 with GST fusion protein of PAK1 Rac-binding domain, and by staining with anti-Rac antibody.

C is a picture showing the investigation of cell polarization and actin polymerization by staining BEα16-3, 17-11, 84-3 with propidium iodide and phalloidin.

Figure 3:
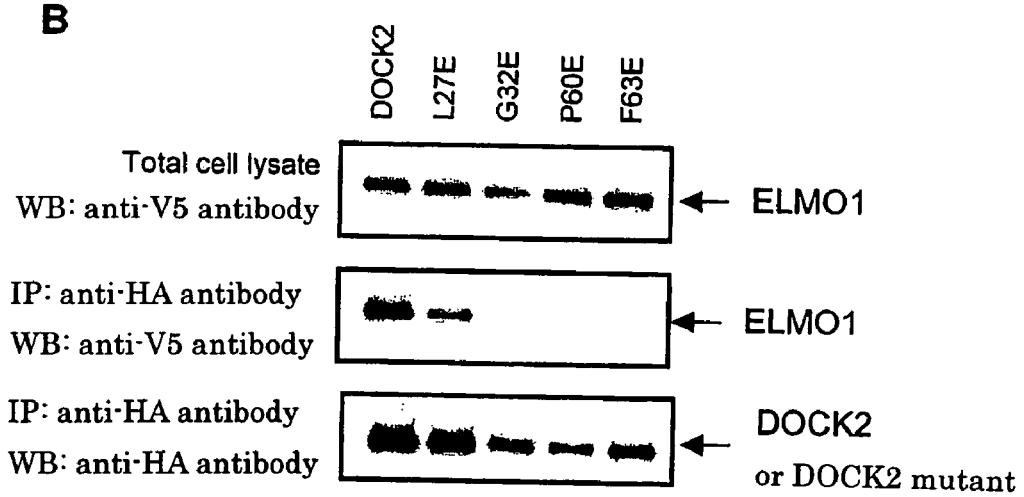

FIG. 3 is a picture showing that DOCK 2 associates with ELMO1 via its SH3 domain.

A is a figure showing the amino acid sequence 10-89 including DOCK2 SH3 domain SEQ ID NO: 8). Amino acid residues substituted to glutamic acid are shown in bold letter.

B is a figure showing the analysis of the binding of DOCK2 with ELMO1 by immunoprecipitation and Western Blot method, by transfecting genes encoding DOCK2 or DOCK2 SH3-deleted mutants to 293T cells with PcDNA ELMO1-V5 and by collecting the cells 48 hours later. Types of samples used for analysis, antibodies used for immunoprecipitation and Western Blot are shown on the left side.

Figure 4:
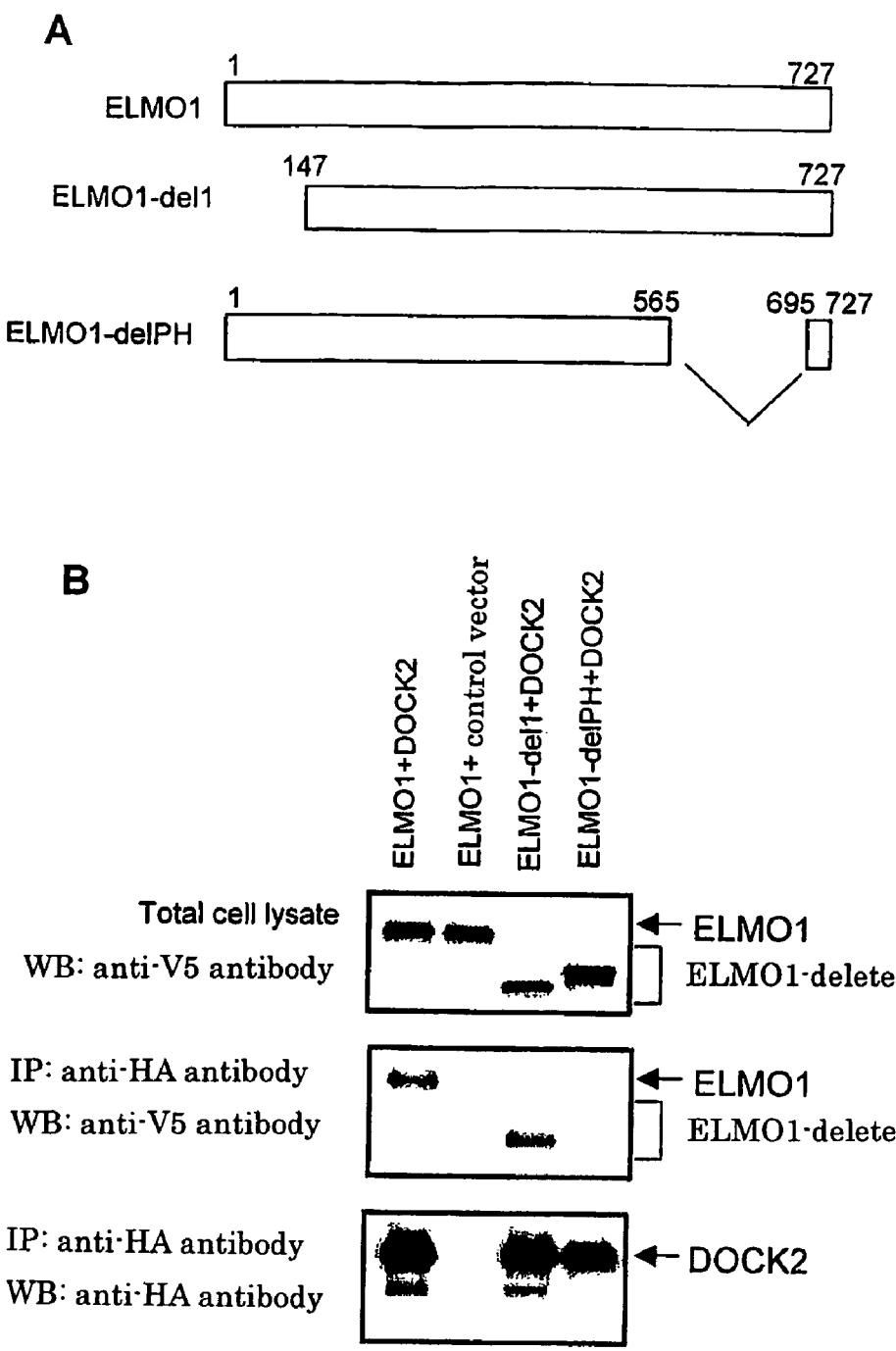

FIG. 4 is a figure showing that ELMO1 is bound with DOCK2 at its C terminus domain.

A is a view showing a frame format of the structure of ELMO1 and of ELMO1-deleted mutants used in this experiment.

B is a figure showing the analysis of the binding of ELMO1 with DOCK2 by immunoprecipitation and Western Blot method, by transfecting genes encoding ELMO1 or ELMO1-deleted mutants to 293T cells with PcDNA DOCK2-HA or a control vector and by collecting the cells 48 hours later. Types of samples used for analysis, antibodies used for immunoprecipitation and Western Blot are shown on the left side.

Figure 5:
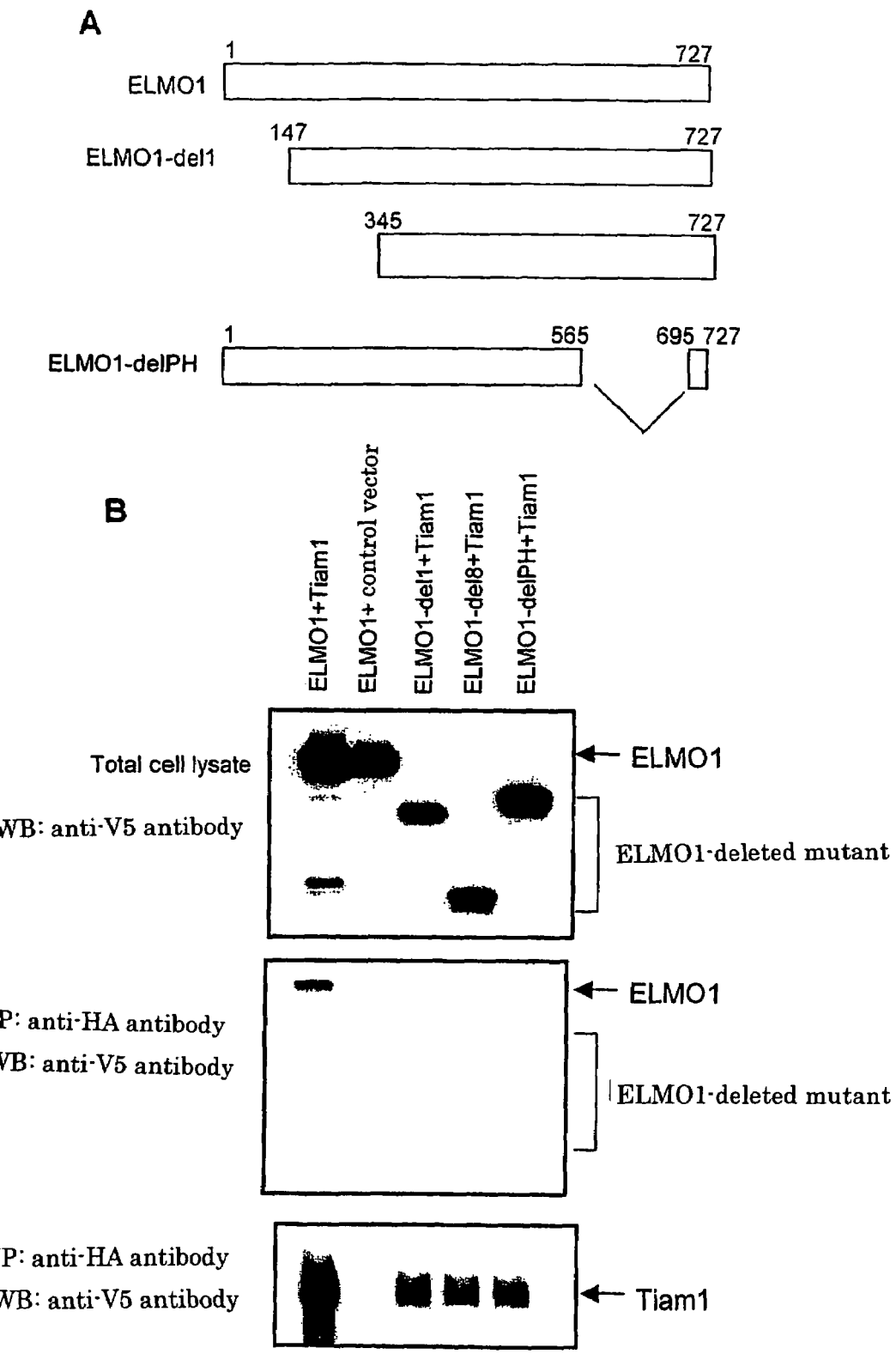

FIG. 5 is a figure showing that ELMO1 is bound to Tiam1 at its N terminus domain.

A is a view showing a frame format of the structure of ELMO1 and of ELMO1-deleted mutants used in this experiment.

B is a figure showing the analysis of the binding with Tiam1 by immunoprecipitation and Western Blot method, by transfecting genes encoding ELMO1 or ELMO1-deleted mutants to 293T cells with PCI Tiam1-HA or a control vector and by collecting the cells 48 hours later. Types of samples used for analysis, antibodies used for immunoprecipitation and Western Blot are shown on the left side.

Figure 6:
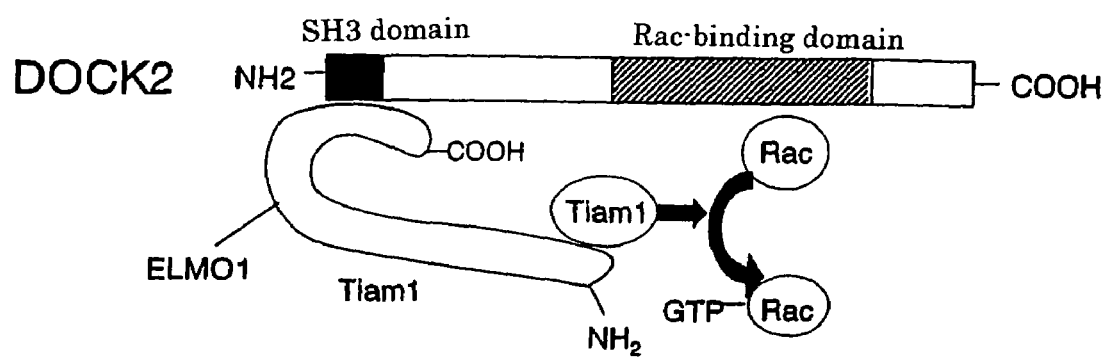

FIG. 6 is a schematical view of the Rac-activating mechanism by DOCK2.

It is a figure showing that DOCK2 activates Rac via ELMO1 by recruiting Tiam1 functioning as GEF of Rac.

BEST MODE OF CARRYING OUT THE INVENTION

As for the method for screening a substance interfering in the association of DOCK2 and ELMO of the present invention, there is no specific limitation as long as it is a method comprising the steps of contacting DOCK2, ELMO and a test substance, and then estimating the level of formation of the association of DOCK2 and ELMO; a method comprising the steps of contacting SH3 domain of DOCK2, ELMO and a test substance, and then estimating the level of formation of the association of SH3 domain of DOCK2 and ELMO; a method comprising the steps of contacting DOCK2, C terminus domain of ELMO and a test substance, and then estimating the level of formation of the association of DOCK2, C terminus domain of ELMO; a method comprising the steps of contacting SH3 domain of DOCK2, C terminus domain of ELMO, and a test substance, and then estimating the level of formation of the association of SH3 domain of DOCK2, C terminus of ELMO. Moreover, as for the above-mentioned DOCK2 or its SH3 domain and/or ELMO or its C terminus domain, a fusion protein or a fusion peptide wherein these and marker protein and/or peptide tag are bound can be used. Moreover, as for the above ELMO, ELMO1, ELMO2, ELMO3 can be specifically exemplified, and ELMO1 can be preferably exemplified.

As for the above SH3 domain of DOCK2, a DOCK2 mutant having a function to associate with ELMO, and that is a peptide containing a whole or a part of SH3 domain of DOCK2 can be exemplified, and specific examples include DOCK2N comprising amino acid residue 1-502 of DOCK2 and DOCK2ΔC comprising amino acid residue 1-1311 of DOCK2. Furthermore, as for the above C terminus domain of ELMO, a mutant of ELMO having the function to associate with SH3 domain of DOCK2, and that is a peptide containing a whole or a part of C terminus domain of ELMO can be exemplified, and specific examples include ELMO1-del1 comprising amino acid residue 147-727 of ELMO1, and ELMO1-del8 comprising amino acid residue 345-727 of ELMO1. Hereinafter, DOCK2 and the above SH3 domain of DOCK2 can be referred together to as "DOCK2 and the like", and ELMO such as ELMO1 and the above C terminus domain of ELMO can be referred together to as "ELMO and the like".

The above DOCK2 mutant or ELMO mutant can be prepared by modifying DOCK2 genes or ELMO genes according to a common procedure. As for DOCK2 genes, Hch (mouse DOCK2) genes (GenBank Accession No. AY027438; Nature, Vol 412, 23 August, 826-831, 2001) and human DOCK2 genes (XM_047961; DNA Res. 3, 321-329) can be specifically exemplified, but the origin of DOCK2 genes is not limited to mouse, human and the like. Moreover, as for ELMO genes such as ELMO1, besides mouse ELMO1 genes (AF398883; Cell, Vol. 107 (1), 27-41, 2001) and human ELMO1 genes (AF398885; Cell, Vol. 107(1) 27-41, 2001), ELMO2 genes (human AF398886, mouse AF398884), ELMO3 genes (human NM_024712) can be specifically exemplified. However, the origin of DOCK2 and ELMO genes is not limited to mouse, human and the like. Additionally, the amino acid sequence of mouse DOCK2, human DOCK2, mouse ELMO1, and human ELMO1 are shown as Seq. ID Nos. 1, 2, 3 and 4, respectively.

As for a marker protein in a fusion protein or fusion peptide wherein the above DOCK2 and the like or ELMO and the like are bound with a marker protein and/or peptide tag, there is no specific limitation as long it is a marker protein conventionally known, and alkaline phosphatase, Fc domain of an antibody, HRP, and GFP can be exemplified. Moreover, as for a peptide tag, examples include peptide tags conventionally known, including epitope tags such as HA, FLAG and Myc; affinity tag such as GST, maltose-binding protein, biotinylated peptide and oligo-histidine. The fusion protein or fusion peptide can be prepared by a common procedure, and can separate/fractionate fusion protein or fusion peptide with DOCK2 and the like, ELMO1 and the like and HA-tag, by using specific antibody against HA tag.

In the method for screening a substance interfering in the association of DOCK2 and ELMO such as ELMO1, as for a method for contacting DOCK2 and the like, ELMO and the like, and a test substance, there is no specific limitation as long as it is a contacting method that can evaluate the level of the formation of the association of DOCK2 and the like and ELMO and the like, and examples include a method for contacting DOCK2 and the like and ELMO and the like, in the presence of a test substance in a cell-free system; a method for introducing an expression vector integrated with ELMO and the like or genes encoding ELMO and the like, in a cell expressing DOCK2 and the like together with a test substance; a method for introducing an expression vector integrated with DOCK2 and the like or genes encoding DOCK2 and the like, in a cell expressing ELMO and the like together with a test substance; or a method for introducing an expression vector integrated with DOCK2 and the like or genes encoding DOCK2 and the like, an expression vector integrated with EOMO and the like or genes encoding ELMO and the like, and a test substance, in a cell not expressing DOCK2 and the like nor ELMO and the like.

As for cells used for contacting with the above test substance, bacterial prokaryotic cells such as *E. Coli, streptomyces, Bacillus subtilis, Streptococcus* and *Staphylococcus*; eukaryotic cells such as yeast and *Aspergillus*; insect cells such as *Drosophila* S2 and *Spodoptera* Sf9; plant and animal cells such as L cells, CHO cells, COS cells, HeLa cells, C127 cells and BALB/c3T3 cells (including mutant strain lacking dihydrofolate reductase or thymidine kinase), BHK21 cells, HEK293 cells, Bowes melanoma cells and oocytes can be exemplified, and animal cells are preferable. Moreover, as for the method for introducing DOCK2 and the like or ELMO and the like in these cells, besides the above methods for introducing genes, a noncytotoxcic reagent such as Chariot (Active Motif) that can form a non-covalent binding with an enormous molecule, change the structure of an enormous molecule such as protein, and that can deliver the enormous molecule such as protein into the cells, can be used.

As for the above expression vector, expression vector for animal cells are preferable, and examples of the expression vector for animal cells include: expression system derived from chromosome, episome, and virus; for example vectors derived from bacterial plasmid, yeast plasmid, papovavirus such as SV40, vaccinia virus, adenovirus, fowl poxvirus, pseudorabies virus, lentivirus, and retrovirus; vectors derived from bacteriophage, transposon, or from combination thereof, for example those derived from plasmid and bacteriophage elements, such as cosmids and phagemids. These expression systems can include regulatory sequences that not only induce expression but also regulate expression. Moreover, liposome can be used in place of expression vectors for animal cells. Further, the introduction of the expression vectors for animal cells into cells can be performed by a method described in various standard laboratory manuals such as Davis et al. (BASIC METHODS IN MOLECULAR BIOLOGY, 1986) and Sambrook et al. (MOLECULAR CLONING: A LABORATORY MANUAL, $2^{nd}$ Ed., Cold Spring Harbor Laboratory Press, Cold Spring Harbor, N.Y., 1989), and examples include calcium phosphate transfection, DEAE-dextran mediated transfection, transvection, microinjection, cationic lipid mediated transfection, electropolation, transduction, scrape loading, ballistic introduction, and infection.

In the method for screening a substance interfering the association of DOCK2 and ELMO such as ELMO1 of the present invention, as for the method for estimating the level of formation of the association of DOCK2 and the like and ELMO and the like, a method for measuring/estimating immunochemically the level of formation of the association of DOCK2 and the like and ELMO and the like, by acting an antibody against ELMO and the like to DOCK2 and the like being separated/fractionated, or by acting an antibody against DOCK2 and the like to ELMO and the like being separated/fractionated, can be exemplified. To separate/fractionate DOCK2 and the like or ELMO and the like, specific antibodies against DOCK2 and the like or ELMO and the like or tag-specific antibodies can be used. Moreover, yeast two hybrid system that can detect protein-protein interaction by using a minute amount of protein and without labeling; or a biosensor using the surface plasmon resonance reaction that can observe at real time as a surface plasmon resonance signal; or a method for measuring/estimating the level of formation of the association by using NMR method that can detect the change of tertiary structure, can be also exemplified. Moreover, publicly known methods for searching interacting protein, such as far western method using *E. coli* expression system and a method using affinity chromatography can be exemplified.

In the method for screening a substance interfering in the association of DOCK2 and ELMO of the present invention, as another method to estimate the level of formation of the association of DOCK2 and the like and ELMO and the like, an estimation method by detecting a GTP-binding form of activated Rac can be exemplified. To detect activated Rac, a pull-down method using GST fusion protein of PAK1 Rac-binding domain can be used.

As for samples to be tested in the method for screening a substance interfering in the association of DOCK2 and ELMO of the present invention, for example, peptides, proteins, synthesized compounds, microbial fermented materials, marine organism extracts, plant extracts, prokaryotic cells extract, eukaryotic unicellular extract, animal cells extract or library thereof can be exemplified. Furthermore, in the method for screening a substance interfering in the association of DOCK2 and ELMO of the present invention, control experiment can be carried out simultaneously. As for control, negative control that does not affect the formation of association of DOCK2 and the like and ELMO and the like, and/or positive control that affect the formation of association of DOCK2 and the like and ELMO and the like can be used.

As for the above substances interfering in the association of DOCK2 and ELMO, substances promoting or suppressing the function of regulating lymphocyte migration, particularly a substance suppressing the function of regulating lymphocyte migration such as substances inhibiting the binding of DOCK2 and ELMO. As for the function of regulating lymphocyte migration, there is no specific limitation as long as it is a function regulating the mobility of lymphocytes based on the expression of DOCK2 genes. Examples include a function promoting cytoskeletal reorganization, in particular actin polymerization in lymphocytes by activating Rac and making a Rac-GTP binding; a function of migrating lymphocytes in response to stimulation of chemokines such as SLC, SDF-1, and BLC; homing function to a secondary lymphoid organ such as spleen, lymph nodes, payer's notch and the like; function of transferring mature thymus T cells to peripheral blood in response to ELC chemokine stimulation; or a function of migrating $CD4^+CD8^+$ immature thymus cells in response to SDF-1 chemokine stimulation.

The present invention relates also to a method for screening a substance interfering in the association of ELMO and GDP/GTP exchange factor (GEF), or to a method for screening a substance promoting or suppressing Rac activation. As for the method for screening a substance interfering in the association of ELMO and GEF, there is no specific limitation as long as it is a method comprising the steps of contacting ELMO, GEF, and a test substance, and then estimating the level of formation of association of ELMO and GEF; or a method comprising the steps of contacting N terminus domain of ELMO, GEF and a test substance, and then estimating the level of formation of association of N terminus domain of ELMO and GEF. Moreover, as for the method for screening a substance promoting or suppressing Rac activation, there is no specific limitation as long as it is a method comprising the steps of contacting DOCK2, ELMO, GEF and a test substance, or by contacting SH3 domain of DOCK2, ELMO, GEF and a test substance, and then estimating the level of formation of association of DOCK2 and ELMO, or the level of formation of association of ELMO and GEF. Further, as for the above ELMO, ELMO bound with DOCK2 can be used.

As for the above ELMO, examples include ELMO1, ELMO2, ELMO3, and among these, ELMO1 can be preferably exemplified. Moreover, as for the above GEF, Rac-specific GDP/GTP exchange factors such as Tiam1, Tiam2, Vav1, Vav2, Vav3, Trio, STEF, P-Rex1 are preferable, and among these, Tiam1 can be preferably exemplified. As for the above Tiam1 gene, mouse Tiam1 gene (NM_009384; Cell Vol. 77(4), 537-549, 1994), human Tiam1 gene (NM_003253; Oncogene Vol. 10(7), 1371-1376, 1995) can be exemplified, but the origin of Tiam1 gene is not limited to mouse, human and the like. Amino acid sequences of mouse Tiam1, human Tiam1 are shown in Seq. ID. Nos. 5 and 6, respectively.

Methods used for the above method for screening a substance interfering in the association of DOCK2 and ELMO, including the above method for screening a substance interfering in the association of ELMO and GEF, or a method for estimating the level of formation of association of ELMO and GEF, a method for estimating the level of formation of association of DOCK2 and ELMO, a method of using ELMO fused with other peptides, or its N terminus, and GEF, in the method for screening a substance for promoting or suppressing Rac activity, can be applied accordingly.

By using the method for screening a substance interfering in the association of DOCK2, ELMO such as ELMO1, the method for screening a substance interfering in the association of ELMO and GEF, the method for screening a substance promoting or suppressing Rac activation of the present invention, particularly the method for screening a substance promoting or suppressing the function of regulating lymphocyte migration, screening of preventive/therapeutic agents of immune related diseases such as allergy, autoimmune diseases, GvH, graft rejection targeting DOCK2 can be possible. As it can be anticipated that substances suppressing the function of regulating lymphocyte migration obtained by the method for screening a substance promoting or suppressing the function of regulating lymphocyte migration, such as anti-DOCK2 SH3 domain antibody, DOCK2 SH3 domain-binding molecule (including low molecular compounds), antisense strand of DOCK2 gene, antibodies recognizing specifically the DOCK2 SH3 domain-binding site of C terminus domain of ELMO such as ELMO1, molecules binding to the DOCK2 SH2 domain-binding site of C terminus domain of ELMO such as ELMO1 (including low molecular compounds), antibodies recognizing specifically GEF-binding site such as Tiam1 of N terminus domain of ELMO such as ELMO1, molecules binding to GEF-binding site such as Tiam1 of N terminus domain of ELMO such as ELMO1 (including low molecular compound), or antisense strand of ELMO such as ELMO1, can suppress artificially lymphocyte mobility, the possibility for these suppressive substances to be a therapeutic agent against immune-related diseases such as allergy, autoimmune diseases, GvH, graft rejection is high. When the therapeutic agent is used as drugs, various prescribed compounds such as pharmaceutically acceptable normal carrier, bonding agent, stabilizing agent, excipient, diluent, pH buffer agent, disintegrator, solubilizer, dissolving adjuvant, isotonic agent can be added, and can be administered by an administration form used generally, for example orally in formulation form such as powder, granule, capsule, syrup, and suspending agent, or parenterally in form of injection those formulated in form of solution, emulsion, suspending solution and the like.

Moreover, when using the method for screening a substance interfering in the association of DOCK2 and ELMO1, the method for screening a substance interfering in the association of ELMO1 and Tiam1, the method for screening a substance promoting or suppressing Rac activity of the present invention, in particular the method for screening a substance promoting the function of regulating lymphocyte migration, cytoskeletal reorganization is promoted by activating Rac, and thus, screening of preventive/therapeutic agents against diseases caused by suppression of lymphocyte migration, such as various cancers, or immunodeficiency caused by drugs/irradiation, can be possible.

Furthermore, as for the method for screening a substance inhibiting DOCK2 function of the present invention, examples include a method making the N terminus domain of DOCK2 including SH3 domain as target, comprising the steps of contacting SH3 domain of DOCK2 and the SH3 domain-binding protein and a test substance, and then estimating the level of formation of association of DOCK2 and SH3 domain-binding protein; and a method by using transgenic cell line expressing full length DOCK2 and DOCK2-deleted mutant, measuring/estimating the level of Rac activation in these cell lines, identifying the functional domain of DOCK2, searching a molecule associated with functional domain that associates with the functional domain, contacting the functional domain of DOCK2, the molecule associated with functional domain and a test substance, and estimating the level of formation of association of functional domain of DOCK2 and molecule associated with the functional domain. As for the method for contacting with a test substance, the method for estimating the level of formation of association, or the method for measuring the level of Rac activation, the methods mentioned above can be used. As for the method for identifying the functional domain of DOCK2, or for the preparation of transgenic cell line expressing full length DOCK2 and DOCK2-deleted mutant, methods described in the following examples can be used.

In the following, the present invention will be explained in detail by reference to the examples, while the technical scope of the present invention is not limited to these examples.

EXAMPLE 1

Binding of N Terminus Domain of DOCK2 and ELMO 1

Figure 1:
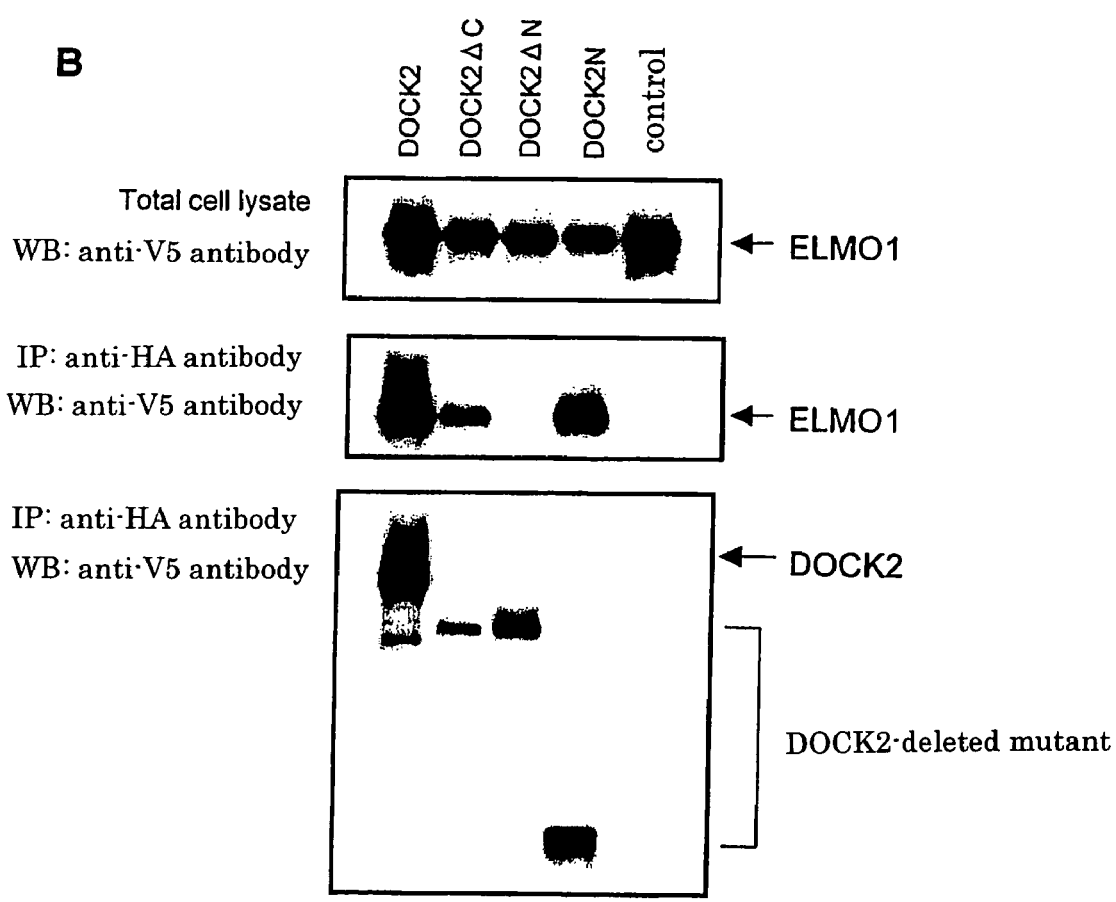
FIG. 1 is a figure showing that DOCK2 binds with ELMO1 at its N terminus domain.

Recently, CED-12 has been identified as a molecule that associates with CED-5 and regulates cytoskeleton in nematodes, and ELMO1 has been reported as its mammal homologue (Cell 107, 27-41, 2001). Therefore, in order to investigate whether DOCK2 binds with ELMO1 or not, by using PcDNA/His max vector (Invitrogen), gene constructs encoding full length DOCK2 or various DOCK2-deleted mutants in which HA tag (YPYDVPDYA: Seq. ID No. 7) is introduced at the C terminus (PcDNA DOCK2-HA, PcDNA DOCK2 N-HA, PcDNA DOCK2ΔC-HA, PcDNA DOCK2ΔN-HA), were constructed. Then, the gene constructs were introduced into 293T cells (provided by Dr. Shinji Hatakeyama, Kyushu University) together with a gene in which ELMO1 cDNA is introduced into PcDNA V5-His vector (Invitrogen) (PcDNA ELMO1-V5). DOCK2 construct was prepared from genes isolated by the present inventors (Nature, 412, 826-831, 2001), and ELMO1 construct was prepared from mouse tissue cDNA by PCR according to a common method. The genes encoding the used DOCK2-deleted mutant are as follows, and they are shown schematically in FIG. 1.
1) PcDNA DOCK2 N-HA; genes encoding amino acid residue 1-502 of DOCK2
2) PcDNA DOCK2ΔC-HA; genes encoding amino acid residue 1-1311 of DOCK2
3) PcDNA DOCK2ΔN-HA; genes encoding amino acid residue 505-1828 of DOCK2

The cells were collected 48 hours after gene introduction, dissolved with Lysis buffer (Cell signaling), and analysed by Western Blot method using anti-V5 antibody (Invistrogen) to immunoprecipitants by total cell lysate and anti-HA antibody (Roche). For each of total cell lysate, a band of approximately 100-KD corresponding to ELMO1 was detected for anti-V5 antibody (FIG. 1B; top). However, for the immunoprecipitants, a band corresponding to ELMO1 was detected, when genes encoding full length DOCK2, DOCK2ΔC and DOCK2 N, while no band was detected when DOCK2ΔN lacking amino acid residues from N terminus to 504 of DOCK2 (FIG. 1B; lower figure of the middle line). From these results, it has been clarified that DOCK2 associates with ELMO1 in the domain of amino acid residues from its N terminus to 502.

EXAMPLE 2

Rac Activation in DOCK2ΔN Lacking the N Terminus Domain

To clarify the influence of the association with ELMO1 to the function of DOCK 2, gene constructs encoding full length DOCK2 and a mutant lacking 504 amino acid residues of the N terminus of DOCK2 (DOCK2ΔN) were constructed by using PBJ1 vector. Then, a stable transgenic cell strain was established by introducing the gene constructs into the T cell strain, BEα16-3 (provided from National Jewish Center, Dr. Philppa Marrack), wherein the expression of DOCK 2 gene is deleted. N3-5 is a wild-type T cell strain expressing DOCK2, and 17-11 (Nature, 412, 826-831, 2001) and 84-3 are transgenic cell strains expressing full length DOCK2 and DOCK2ΔN, respectively, that the present inventors have established. In the Western Blot analysis using anti-DOCK2 polyclonal antibody that the present inventors have prepared, the expression of DOCK2 and DOCK2ΔN was approximately the same in 17-11 and 84-3 (FIG. 2A). Therefore, by targeting to 17-11 and 84-3, Rac activity in these cell strains was compared and analyzed by pull-down method using GST fusion protein of PAK1 Rac binding domain. In 17-11 expressing full length DOCK2, GTP-binding form of activated Rac was easily detected, whereas in 84-3 expressing DOCK2ΔN lacking the binding site with ELMO 1, Rac activating ability was significantly decreased (FIG. 2B). From the nuclear stain of 17-11 and 84-3 with PI (propidium iodide), it has been revealed that in any case, the nucleus is eccentrically located, in other words, that cell polarization is performed, which is different from BEα16-3, the parent cell strain (FIG. 2C; top). On the contrary, when these cells are stained with phalloidin, which is a probe for F-actin, actin polymerization was observed only for 17-11, and not in 84-3, as in the case of Beα16-3, wherein the DOCK2 expression is deleted (FIG. 2C; bottom). From these results, the association of DOCK2 and ELMO1 has been suggested to be extremely crucial to the full activation of Rac as well as to cytoskeletal reorganization, relating thereof. From the above, it has been clarified that in DOCK2ΔN, lacking N terminus domain being essential for the binding with ELMO1, the Rac-activating ability is significantly decreased, and that actin polymerization cannot be induced.

EXAMPLE 3

Association with ELMO1, via SH3 Domain of DOCK2

SH (Src-homolgy)3 domain known to be related with the protein-protein interaction is encoded at the N-terminus of DOCK2. As it was found that 502 amino acid residues at the N terminus of DOCK2 are crucial for the association with ELMO1, it was investigated if it is mediated by SH3 domain. Amino acid residues commonly conserved exist in the SH3 domain. Therefore, gene constructs encoding various DOCK2 SH3 mutants wherein HA tag is introduced into C terminus by using PcDNA/His max vector, were constructed. Then, these were introduced into 293T cells with PcDNA ELMO1-V5, and were analyzed in the same manner as in FIG. 1B. Genes encoding DOCK2 SH3 mutant are as follows:
1) PcDNA L27E-HA; gene encoding mutant wherein leucin at the 27 position of DOCK2 is substituted to glutamic acid
2) PcDNA G32E-HA; gene encoding mutant wherein glycine at the 32 position of DOCK2 is substituted to glutamic acid
3) PcDNA P60E-HA; gene encoding mutant wherein poline at the 60 position of DOCK2 is substituted to glutamic acid
4) PcDNA F63E-HA; gene encoding mutant wherein phenylalanine at the 63 position of DOCK2 is substituted to glutamic acid Amino acid sequence from 10-89 including DOCK2 SH3 domain is shown in FIG. 3A. For each of total cell lysate, an approximately 100-KD band corresponding to ELMO1 for anti-V5 antibody was detected (FIG. 3B; top). However, when targeting to immunoprecipitants using anti-HA antibody, the band corresponding to ELMO1 was not detected except for those introduced with PcDNA DOCK2-HA and PcDNA L27E-HA (FIG. 3B; middle). On the other hand, when any one of the genes has been introduced, DOCK2 and DOCK2 SH3 mutant expressions were almost of the same level (FIG. 3B; lower). The above results show that the association of DOCK2 and ELMO1 is completely inhibited by substituting a single amino acid of SH3 domain. Therefore, it has been clarified that DOCK2 is bound to ELMO1 via its SH3 domain.

EXAMPLE 4

Binding of C Terminus Domain of ELMO1 and DOCK2

Next, to identify the functional domain of ELMO1 binding with DOCK2, gene constructs encoding various ELMO1-deleted mutants were constructed by using PcDNA V5His vector, and were analyzed by introducing these into 293T cells with PcDNA DOCK2-HA. Genes herein used, encoding ELMO1-deleted mutants are as follows, which are shown schematically in FIG. 4A.
1) PcDNA ELMO1-del1-V5; gene encoding amino acid residues at the position 147-727 of ELMO1
2) PcDNA ELMO1-del8-V5; gene encoding amino acid residues at the position 345-727 of ELMO1
3) PcDNA ELMO1-del10-V5; gene encoding amino acid residues at the position 1-613 of ELMO1

For each of the total cell lysate, band corresponding to ELMO1 or its deleted mutant was detected with anti-V5 antibody (FIG. 4B; top). However, as for immunoprecipitants with anti-HA antibody, bands reacting to anti-V5 antibody were observed when genes encoding full length ELMO1, ELMO1-dell and ELMO1-del8 were introduced, but not when PcDNA ELMO1-del10 lacking amino acid residues at the position 614-727 of ELMO1, was expressed (FIG. 4B; middle, bottom). From these, C terminus domain including amino acid residues at the position 614-727 of ELMO1 was revealed to be crucial for the association of DOCK2 SH3 domain. From these results, it has been clarified that ELMO1 was bound with DOCK2 in its C terminus domain.

EXAMPLE 5

Binding of N Terminus Domain of ELMO1 and Tiam1

Tiam 1 has been identified as a molecule that determines the invasion of thymoma cell lines, and is known to function as Rac-specific GDP/GTP exchange factor (GEF) (Cell 77, 537-549, 1994; Nature 375, 338-340, 1995). As the association of DOCK2 and ELMO1 is necessary for the full activation of Rac, it has been estimated that DOCK2 might recruit Tiam1 via ELMO1. To investigate this assumption, from a Tiam1 gene amplified by PCR method from cDNA derived from mouse organs, a construct encoding Tiam1 wherein HA tag was introduced at its C terminus (PCI Tiam1-HA) was constructed with the use of PCI vector (Promega), introduced into 293T cells with genes encoding full length or various ELMO1-deleted mutants (PcDNA ELMO1-V5, PcDNA ELMO1-delPH-V5, PcDNA ELMO1-del8-V5, PcDNA ELMO1-del1), and was then analyzed. PcDNA ELMO1-delPH-V5 is a gene encoding amino acid residues at the position 1-565 and 695-727 of ELMO1. ELMO1-deleted mutants herein used are shown schematically in FIG. 5A. For each of the total cell lysate, a band corresponding to ELMO1 or its deleted mutant was detected with anti-V5 antibody (FIG. 5B; top). In immunoprecipitants with anti-HA antibody, when PcDNA ELMO1-V5 and PcDNA ELMO1-delPH-V5 were introduced, bands reacting to anti-V5 antibody were detected (FIG. 5B; middle, bottom). This shows that Tiam1 binds with ELMO1. However, as for mutants lacking amino acid residues from N terminus to 146, or to 344, of ELMO1, such binding was not observed (FIG. 5B; middle, bottom). From these results, it has been revealed that ELMO1 is associated with Tiam1 at its N terminus.

From the above, the following has been revealed:
1) DOCK2 binds to the C terminus domain of ELMO1 via SH3 domain
2) ELMO1 binds with Tiam1 via its N terminus domain
3) Rac-activating ability is significantly decreased in DOCK2 mutants that cannot bind with ELMO1.

Therefore, it has been shown that DOCK2 activates Rac by recruiting Tiam1 that functions as GEF of Rac, via ELMO1 (FIG. 6).

As autoimmune diseases and graft rejection are induced when lymphocytes invate into the target tissues, DOCK2 signaling should be the excellent target to treat or prevent these diseases or pathologic conditions. The finding of the invention shows that interaction between molecules such as DOCK2, ELMO1 and Tiam1 regulate Rac activation that is essential for cell mobility. Therefore, it can be thought that by blocking the intermolecular interaction, the invasion of lymphocytes can be inhibited. Therefore, these intermolecular interactions are anticipated to be the target of drug discovery heading to the development of method for treating or preventing autoimmune diseases or graft rejection.

INDUSTRIAL APPLICABILITY

According to the present invention, it is possible to elucidate the interaction between molecules of DOCK2, and to provide a substance controlling lymphocyte migration and a method to regulate lymphocyte migration targeting DOCK2. Moreover, according to the present invention, it is possible to provide preventive or therapeutic agents of autoimmune diseases or graft rejections after implantation.

The invention claimed is:

1. A method for screening a substance interfering in the association of DOCK2 and ELMO, comprising the steps of contacting DOCK2, ELMO and a test substance, and then estimating the level of interference of association of DOCK2 and ELMO by detecting a GTP-binding form of activated-Rac.

2. The method for screening a substance interfering in the association of DOCK2 and ELMO according to claim 1, wherein the substance interfering in the association of DOCK2 and ELMO is a substance promoting or suppressing the function of regulating lymphocyte migration.

3. The method for screening a substance interfering in the association of DOCK2 and ELMO according to claim 1, wherein the substance interfering in the association of DOCK2 and ELMO is a substance inhibiting the binding of DOCK2 and ELMO.

4. The method for screening a substance interfering in the association of DOCK2 and ELMO according to claim 1, wherein ELMO is ELMO1.

5. A method for screening a substance interfering in the association of DOCK2 and ELMO, comprising the steps of contacting an SH3 domain of DOCK2, ELMO and a test substance, and then estimating the level of interference of association of the SH3 domain of DOCK2 and ELMO by detecting a GTP-binding form of activated-Rac.

6. A method for screening a substance interfering in the association of DOCK2 and the C terminus domain of ELMO, comprising the steps of contacting DOCK2, the C terminus domain of ELMO and a test substance, and then estimating the level of interference of association of DOCK2 and the C terminus domain of ELMO by detecting a GTP-binding form of activated-Rac.

7. A method for screening a substance interfering in the association of DOCK2 and ELMO, comprising the steps of contacting an SH3 domain of DOCK2, the C terminus domain of ELMO and a test substance, and then estimating the level of interference of association of the SH3 domain of DOCK2 and the C terminus domain of ELMO by detecting a GTP-binding form of activated-Rac.

* * * * *

UNITED STATES PATENT AND TRADEMARK OFFICE
CERTIFICATE OF CORRECTION

PATENT NO. : 7,541,153 B2  Page 1 of 1
APPLICATION NO. : 10/535223
DATED : June 2, 2009
INVENTOR(S) : Fukui et al.

It is certified that error appears in the above-identified patent and that said Letters Patent is hereby corrected as shown below:

On the cover page, item

[*] Notice: Subject to any disclaimer, the term of this patent is extended or adjusted under 35 USC 154(b) by (325) days Delete the phrase "by 325 days" and insert -- by 371 days --

Signed and Sealed this

Twentieth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,541,153 B2
APPLICATION NO. : 10/535223
DATED : June 2, 2009
INVENTOR(S) : Fukui et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (325) days Delete the phrase "by 325 days" and insert -- by 697 days --

Signed and Sealed this

Twentieth Day of April, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 1828
<212> TYPE: PRT
<213> ORGANISM: Mus musculus

<400> SEQUENCE: 1

Met Ala Pro Trp Arg Lys Thr Asp Lys Glu Arg His Gly Val Ala Ile
 1               5                  10                  15

Tyr Asn Phe Gln Gly Ser Glu Ala Gln His Leu Thr Leu Gln Ile Gly
            20                  25                  30

Asp Val Val Arg Ile Gln Glu Thr Cys Gly Asp Trp Tyr Arg Gly Tyr
        35                  40                  45

Leu Ile Lys His Lys Leu Ser Gln Gly Ile Phe Pro Thr Ser Phe Ile
    50                  55                  60

His Leu Lys Glu Val Thr Val Glu Lys Arg Arg Asn Ile Glu Asn Ile
65                  70                  75                  80

Ile Pro Ala Glu Ile Pro Leu Ala Gln Glu Val Thr Thr Thr Leu Trp
                85                  90                  95

Glu Trp Gly Ser Ile Trp Lys Gln Leu Tyr Val Ala Ser Lys Lys Glu
            100                 105                 110

Arg Phe Leu Gln Val Gln Ser Met Met Tyr Asp Leu Met Glu Trp Arg
        115                 120                 125

Ser Gln Leu Leu Ser Gly Thr Leu Pro Lys Asp Glu Leu Lys Glu Leu
    130                 135                 140

Lys Gln Lys Val Thr Ser Lys Ile Asp Tyr Gly Asn Lys Ile Leu Glu
145                 150                 155                 160

Leu Asp Leu Ile Val Arg Asp Glu Asp Gly Asn Ile Leu Asp Pro Asp
                165                 170                 175
```

-continued

```
Lys Thr Ser Val Ile Ser Leu Phe His Ala His Glu Ala Thr Tyr
            180                 185                 190

Lys Ile Thr Glu Arg Ile Lys Glu Glu Met Ser Lys Asp Gln Pro Asp
            195                 200                 205

Tyr Gly Val Tyr Ser Arg Ile Ser Ser Pro Thr His Ser Leu Tyr
            210                 215                 220

Val Phe Val Arg Asn Phe Val Cys Arg Ile Gly Glu Asp Ala Glu Leu
225                 230                 235                 240

Phe Met Ser Leu Tyr Asp Pro His Lys Gln Thr Val Ile Ser Glu Asn
                245                 250                 255

Tyr Leu Val Arg Trp Gly Ser Lys Gly Phe Pro Lys Glu Ile Glu Met
                260                 265                 270

Leu Asn Asn Leu Lys Val Val Phe Thr Asp Leu Gly Asn Lys Asp Leu
            275                 280                 285

Asn Arg Asp Lys Ile Phe Leu Ile Cys Gln Ile Val Arg Ile Gly Lys
            290                 295                 300

Met Asp Leu Lys Asp Ile Asn Ala Lys Lys Cys Thr Gln Gly Leu Arg
305                 310                 315                 320

Arg Pro Phe Gly Val Ala Val Met Asp Ile Thr Asp Ile Ile Lys Gly
                325                 330                 335

Lys Ala Glu Ser Asp Glu Glu Lys Gln His Phe Ile Pro Phe His Pro
            340                 345                 350

Val Ser Ala Glu Asn Asp Phe Leu His Ser Leu Leu Gly Lys Val Ile
            355                 360                 365

Ala Ser Lys Gly Asp Ser Gly Gly Gln Gly Leu Trp Val Thr Met Lys
            370                 375                 380

Met Leu Val Gly Asp Ile Ile Gln Ile Arg Lys Asp Tyr Pro His Leu
385                 390                 395                 400

Val Asp Arg Thr Thr Val Val Ala Arg Lys Leu Gly Phe Pro Glu Ile
                405                 410                 415

Ile Met Pro Gly Asp Val Arg Asn Asp Ile Tyr Ile Thr Leu Leu Gln
            420                 425                 430

Gly Asp Phe Asp Lys Tyr Thr Lys Thr Thr Gln Arg Asn Val Glu Val
            435                 440                 445

Ile Met Cys Val Cys Thr Glu Asp Gly Lys Val Leu Pro Asn Ala Ile
            450                 455                 460

Cys Val Gly Ala Gly Asp Lys Ala Met Asn Glu Tyr His Ser Val Val
465                 470                 475                 480

Tyr Tyr Gln Val Lys Gln Pro Arg Trp Met Glu Thr Val Lys Val Ala
                485                 490                 495

Val Pro Ile Glu Asp Met Gln Arg Ile His Leu Arg Phe Met Phe Arg
            500                 505                 510

His Arg Ser Ser Leu Glu Ser Lys Asp Lys Gly Glu Lys Asn Phe Ala
            515                 520                 525

Met Ser Tyr Val Lys Leu Met Lys Glu Asp Gly Thr Thr Leu His Asp
            530                 535                 540

Gly Tyr His Glu Leu Val Leu Lys Gly Asp Ser Lys Lys Met Glu
545                 550                 555                 560

Asp Ala Ser Ala Tyr Leu Thr Leu Pro Ser Tyr Arg His Pro Val Glu
                565                 570                 575

Asn Lys Gly Ala Thr Leu Ser Arg Ser Ser Ser Val Gly Gly Leu
            580                 585                 590

Ser Val Ser Ser Arg Asp Val Phe Ser Ile Ser Thr Leu Val Cys Ser
```

-continued

```
            595                 600                 605
Thr Lys Leu Thr Gln Asn Val Gly Leu Gly Leu Leu Lys Trp Arg
            610                 615                 620
Met Lys Pro Gln Leu Leu Gln Glu Asn Leu Glu Lys Leu Lys Ile Val
625                 630                 635                 640
Asp Gly Glu Glu Val Val Lys Phe Leu Gln Asp Thr Leu Asp Ala Leu
                    645                 650                 655
Phe Asn Ile Met Met Glu His Ser Gln Ser Asn Glu Tyr Asp Ile Leu
                660                 665                 670
Val Phe Asp Ala Leu Ile Tyr Ile Ile Gly Leu Ile Ala Asp Arg Lys
            675                 680                 685
Phe Gln His Phe Asn Thr Val Leu Glu Ala Tyr Ile Gln Gln His Phe
            690                 695                 700
Ser Ala Thr Leu Ala Tyr Lys Lys Leu Met Thr Val Leu Lys Thr Tyr
705                 710                 715                 720
Leu Asp Thr Ser Ser Arg Gly Glu Gln Cys Glu Pro Ile Leu Arg Thr
                    725                 730                 735
Leu Lys Ala Leu Glu Tyr Val Phe Lys Phe Ile Val Arg Ser Arg Thr
                740                 745                 750
Leu Phe Ser Gln Leu Tyr Glu Gly Lys Glu Gln Met Glu Phe Glu Glu
            755                 760                 765
Ser Met Arg Arg Leu Phe Glu Ser Ile Asn Asn Leu Met Lys Ser Gln
            770                 775                 780
Tyr Lys Thr Thr Ile Leu Leu Gln Val Ala Ala Leu Lys Tyr Ile Pro
785                 790                 795                 800
Ser Val Leu His Asp Val Glu Thr Val Phe Asp Ala Lys Leu Leu Ser
                    805                 810                 815
Gln Leu Leu Tyr Glu Phe Tyr Thr Cys Ile Pro Pro Val Lys Leu Gln
                820                 825                 830
Lys Gln Lys Val Gln Ser Met Asn Glu Ile Val Gln Ser Asn Leu Phe
            835                 840                 845
Lys Lys Gln Glu Cys Arg Asp Ile Leu Leu Pro Val Ile Thr Lys Glu
850                 855                 860
Leu Lys Glu Leu Leu Glu Gln Arg Asp Asp Gly Gln His Gln Ala Glu
865                 870                 875                 880
Lys Lys His Cys Val Glu Leu Leu Asn Ser Ile Leu Glu Val Leu Ser
                    885                 890                 895
Cys Gln Asp Ala Ala Phe Thr Tyr Asp His Ile Gln Glu Ile Met Val
                900                 905                 910
Gln Leu Leu Arg Thr Val Asn Arg Thr Val Ile Thr Met Gly Arg Asp
            915                 920                 925
His Ala Leu Ile Ser His Phe Glu Ala Cys Met Thr Ala Ile Leu Asp
            930                 935                 940
Gln Met Gly Asp Gln His Tyr Ser Phe Tyr Ile Glu Thr Phe Gln Thr
945                 950                 955                 960
Ser Ser Asp Leu Val Asp Phe Leu Met Glu Thr Phe Ile Met Phe Lys
                    965                 970                 975
Asp Leu Ile Gly Lys Asn Val Tyr Pro Gly Asp Trp Met Ala Met Ser
                980                 985                 990
Met Val Gln Asn Arg Val Phe Leu Arg Ala Ile Asn Lys Phe Ala Glu
            995                 1000                1005
Thr Met Asn Gln Lys Phe Leu Glu His Thr Ser Phe Glu Phe Gln Leu
        1010                1015                1020
```

```
Trp Asn Asn Tyr Phe His Leu Ala Val Ala Phe Ile Thr Gln Asp Ser
1025                1030                1035                1040

Leu Gln Leu Glu Gln Phe Thr His Ala Lys Tyr Asn Lys Ile Leu Asn
            1045                1050                1055

Lys Tyr Gly Asp Met Arg Arg Leu Ile Gly Phe Ser Ile Arg Asp Met
        1060                1065                1070

Trp Tyr Lys Leu Gly Gln Asn Lys Ile Cys Phe Ile Pro Gly Met Val
    1075                1080                1085

Gly Pro Ile Leu Glu Met Thr Leu Ile Pro Glu Ala Glu Leu Arg Lys
1090                1095                1100

Ala Thr Ile Pro Ile Phe Phe Asp Met Met Leu Cys Glu Tyr Gln Arg
1105                1110                1115                1120

Thr Gly Ala Phe Lys Lys Phe Glu Asn Glu Ile Ile Leu Lys Leu Asp
            1125                1130                1135

His Glu Val Glu Gly Arg Gly Asp Glu Gln Tyr Met Gln Leu Leu
        1140                1145                1150

Glu Ser Ile Leu Met Glu Cys Thr Ala Glu His Pro Thr Ile Ala Lys
    1155                1160                1165

Ser Val Glu Asn Phe Val Ser Leu Val Lys Gly Leu Leu Glu Lys Leu
1170                1175                1180

Leu Asp Tyr Arg Gly Val Met Thr Asp Glu Ser Lys Asp Asn Arg Met
1185                1190                1195                1200

Ser Cys Thr Val Asn Leu Leu Asn Phe Tyr Lys Asp Asn Asn Arg Glu
            1205                1210                1215

Glu Met Tyr Ile Arg Tyr Leu Tyr Lys Leu Arg Asp Leu His Leu Asp
        1220                1225                1230

Cys Glu Asn Tyr Thr Glu Ala Ala Tyr Thr Leu Leu Leu His Thr Trp
    1235                1240                1245

Leu Leu Lys Trp Ser Asp Glu Gln Cys Ala Ser Gln Val Met Gln Thr
1250                1255                1260

Gly Gln Gln His Pro Gln Thr His Arg Gln Leu Lys Glu Thr Leu Tyr
1265                1270                1275                1280

Glu Thr Ile Ile Gly Tyr Phe Asp Lys Gly Lys Met Trp Glu Glu Ala
            1285                1290                1295

Ile Ser Leu Cys Lys Glu Leu Ala Glu Gln Tyr Glu Met Glu Ile Phe
        1300                1305                1310

Asp Tyr Glu Leu Leu Ser Gln Asn Leu Thr Gln Gln Ala Lys Phe Tyr
    1315                1320                1325

Glu Asn Ile Met Lys Ile Leu Arg Thr Lys Pro Asp Tyr Phe Ala Val
1330                1335                1340

Gly Tyr Tyr Gly Gln Gly Phe Pro Ser Phe Leu Arg Asn Lys Val Phe
1345                1350                1355                1360

Ile Tyr Arg Gly Lys Glu Tyr Glu Arg Arg Glu Asp Phe Gln Met Gln
            1365                1370                1375

Leu Leu Ser Gln Phe Pro Asn Ala Glu Lys Met Asn Thr Thr Ser Ala
        1380                1385                1390

Pro Gly Asp Asp Val Arg Asn Ala Pro Gly Gln Tyr Ile Gln Cys Phe
    1395                1400                1405

Thr Val Gln Pro Val Leu Asp Glu His Pro Arg Phe Lys Asn Lys Pro
1410                1415                1420

Val Pro Asp Gln Ile Ile Asn Phe Tyr Lys Ser Asn Tyr Val Gln Lys
1425                1430                1435                1440
```

Phe His Tyr Ser Arg Pro Val Arg Arg Gly Lys Val Asp Pro Glu Asn
              1445                1450                1455

Glu Phe Ala Ser Met Trp Ile Glu Arg Thr Ser Phe Leu Thr Ala Tyr
        1460                1465                1470

Lys Leu Pro Gly Ile Leu Arg Trp Phe Glu Val Val His Met Ser Gln
    1475                1480                1485

Thr Thr Ile Ser Pro Leu Glu Asn Ala Ile Glu Thr Met Ser Thr Val
1490                1495                1500

Asn Glu Lys Ile Leu Met Met Ile Asn Gln Tyr Gln Ser Asp Glu Ser
1505                1510                1515                1520

Leu Pro Ile Asn Pro Leu Ser Met Leu Leu Asn Gly Ile Val Asp Pro
            1525                1530                1535

Ala Val Met Gly Gly Phe Ala Lys Tyr Glu Lys Ala Phe Phe Thr Glu
        1540                1545                1550

Glu Tyr Ser Arg Glu His Pro Glu Asp Gln Asp Lys Leu Ser His Leu
    1555                1560                1565

Lys Asp Leu Ile Ala Trp Gln Ile Pro Phe Leu Gly Ala Gly Ile Lys
    1570                1575                1580

Ile His Glu Lys Arg Val Ser Asp Asn Leu Arg Pro Phe His Asp Arg
1585                1590                1595                1600

Met Glu Glu Cys Phe Lys Asn Leu Lys Met Lys Val Glu Lys Glu Tyr
            1605                1610                1615

Gly Val Arg Glu Met Pro Asp Phe Glu Asp Arg Arg Val Gly Arg Pro
        1620                1625                1630

Arg Ser Met Leu Arg Ser Tyr Arg Gln Met Ser Val Ile Ser Leu Ala
        1635                1640                1645

Ser Met His Ser Asp Cys Ser Thr Pro Ser Lys Val Pro Ala Glu Ser
    1650                1655                1660

Phe Asp Leu Glu Ser Ala Pro Pro Lys Thr Pro Lys Val Glu Glu Glu
1665                1670                1675                1680

Pro Ile Ser Pro Gly Ser Thr Leu Pro Glu Val Lys Leu Arg Arg Ser
            1685                1690                1695

Lys Lys Arg Thr Lys Arg Ser Ser Val Val Phe Ala Asp Glu Lys Ala
        1700                1705                1710

Ala Thr Glu Ser Asp Leu Lys Arg Leu Ser Arg Lys Gln Glu Phe Met
        1715                1720                1725

Ser Asp Thr Asn Leu Ser Glu His Ala Ala Ile Pro Ala Arg Val Ser
    1730                1735                1740

Ile Leu Ser Gln Met Ser Phe Ala Ser Gln Ser Met Pro Thr Ile Pro
1745                1750                1755                1760

Ala Leu Thr Leu Ser Val Ala Gly Val Pro Gly Leu Asp Glu Ala Asn
            1765                1770                1775

Thr Ser Pro Arg Leu Ser Gln Thr Phe Phe Gln Val Ser Asp Gly Asp
        1780                1785                1790

Lys Lys Thr Leu Lys Lys Lys Val Asn Gln Phe Phe Lys Thr Met
        1795                1800                1805

Leu Ala Ser Lys Ser Ser Glu Glu Ser Lys Gln Ile Pro Asp Phe Leu
    1810                1815                1820

Ser Thr Asn Met
1825

<210> SEQ ID NO 2
<211> LENGTH: 1830
<212> TYPE: PRT

<213> ORGANISM: Homo sapiens

<400> SEQUENCE: 2

Met Ala Pro Trp Arg Lys Ala Asp Lys Glu Arg His Gly Val Ala Ile
1               5                   10                  15

Tyr Asn Phe Gln Gly Ser Gly Ala Pro Gln Leu Ser Leu Gln Ile Gly
            20                  25                  30

Asp Val Val Arg Ile Gln Glu Thr Cys Gly Asp Trp Tyr Arg Gly Tyr
        35                  40                  45

Leu Ile Lys His Lys Met Leu Gln Gly Ile Phe Pro Lys Ser Phe Ile
    50                  55                  60

His Ile Lys Glu Val Thr Val Glu Lys Arg Arg Asn Thr Glu Asn Ile
65                  70                  75                  80

Ile Pro Ala Glu Ile Pro Leu Ala Gln Glu Val Thr Thr Thr Leu Trp
                85                  90                  95

Glu Trp Gly Ser Ile Trp Lys Gln Leu Tyr Val Ala Ser Lys Lys Glu
            100                 105                 110

Arg Phe Leu Gln Val Gln Ser Met Met Tyr Asp Leu Met Glu Trp Arg
        115                 120                 125

Ser Gln Leu Leu Ser Gly Thr Leu Pro Lys Asp Glu Leu Lys Glu Leu
    130                 135                 140

Lys Gln Lys Val Thr Ser Lys Ile Asp Tyr Gly Asn Lys Ile Leu Glu
145                 150                 155                 160

Leu Asp Leu Ile Val Arg Asp Glu Asp Gly Asn Ile Leu Asp Pro Asp
                165                 170                 175

Asn Thr Ser Val Ile Ser Leu Phe His Ala His Glu Glu Ala Thr Asp
            180                 185                 190

Lys Ile Thr Glu Arg Ile Lys Glu Glu Met Ser Lys Asp Gln Pro Asp
        195                 200                 205

Tyr Ala Met Tyr Ser Arg Ile Ser Ser Pro Thr His Ser Leu Tyr
    210                 215                 220

Val Phe Val Arg Asn Phe Val Cys Arg Ile Gly Glu Asp Ala Glu Leu
225                 230                 235                 240

Phe Met Ser Leu Tyr Asp Pro Asn Lys Gln Thr Val Ile Ser Glu Asn
                245                 250                 255

Tyr Leu Val Arg Trp Gly Ser Arg Gly Phe Pro Lys Glu Ile Glu Met
            260                 265                 270

Leu Asn Asn Leu Lys Val Val Phe Thr Asp Leu Gly Asn Lys Asp Leu
        275                 280                 285

Asn Arg Asp Lys Ile Tyr Leu Ile Cys Gln Ile Val Arg Val Gly Lys
    290                 295                 300

Met Asp Leu Lys Asp Thr Gly Ala Lys Lys Cys Thr Gln Gly Leu Arg
305                 310                 315                 320

Arg Pro Phe Gly Val Ala Val Met Asp Ile Thr Asp Ile Ile Lys Gly
                325                 330                 335

Lys Ala Glu Ser Asp Glu Glu Lys Gln His Phe Ile Pro Phe His Pro
            340                 345                 350

Val Thr Ala Glu Asn Asp Phe Leu His Ser Leu Leu Gly Lys Val Ile
        355                 360                 365

Ala Ser Lys Gly Asp Ser Gly Gly Gln Gly Leu Trp Val Thr Met Lys
    370                 375                 380

Met Leu Val Gly Asp Ile Ile Gln Ile Arg Lys Asp Tyr Pro His Leu
385                 390                 395                 400

-continued

```
Val Asp Arg Thr Thr Val Val Ala Arg Lys Leu Gly Phe Pro Glu Ile
                405                 410                 415
Ile Met Pro Gly Asp Val Arg Asn Asp Ile Tyr Ile Thr Leu Leu Gln
            420                 425                 430
Gly Asp Phe Asp Lys Tyr Asn Lys Thr Thr Gln Arg Asn Val Glu Val
            435                 440                 445
Ile Met Cys Val Cys Ala Glu Asp Gly Lys Thr Leu Pro Asn Ala Ile
        450                 455                 460
Cys Val Gly Ala Gly Asp Lys Pro Met Asn Glu Tyr Arg Ser Val Val
465                 470                 475                 480
Tyr Tyr Gln Val Lys Gln Pro Arg Trp Met Glu Thr Val Lys Val Ala
                485                 490                 495
Val Pro Ile Glu Asp Met Gln Arg Ile His Leu Arg Phe Met Phe Arg
            500                 505                 510
His Arg Ser Ser Leu Glu Ser Lys Asp Lys Gly Glu Lys Asn Phe Ala
        515                 520                 525
Met Ser Tyr Val Lys Leu Met Lys Glu Asp Gly Thr Thr Leu His Asp
    530                 535                 540
Gly Phe His Asp Leu Val Val Leu Lys Gly Asp Ser Lys Lys Met Glu
545                 550                 555                 560
Asp Ala Ser Ala Tyr Leu Thr Leu Pro Ser Tyr Arg His His Val Glu
                565                 570                 575
Asn Lys Gly Ala Thr Leu Ser Arg Ser Ser Ser Val Gly Gly Leu
            580                 585                 590
Ser Val Ser Ser Arg Asp Val Phe Ser Ile Ser Thr Leu Val Cys Ser
        595                 600                 605
Thr Lys Leu Thr Gln Asn Val Gly Leu Leu Gly Leu Leu Lys Trp Arg
    610                 615                 620
Met Lys Pro Gln Leu Leu Gln Glu Asn Leu Glu Lys Leu Lys Ile Val
625                 630                 635                 640
Asp Gly Glu Glu Val Val Lys Phe Leu Gln Asp Thr Leu Asp Ala Leu
                645                 650                 655
Phe Asn Ile Met Met Glu His Ser Gln Ser Asp Glu Tyr Asp Ile Leu
            660                 665                 670
Val Phe Asp Ala Leu Ile Tyr Ile Ile Gly Leu Ile Ala Asp Arg Lys
        675                 680                 685
Phe Gln His Phe Asn Thr Val Leu Glu Ala Tyr Ile Gln Gln His Phe
    690                 695                 700
Ser Ala Thr Leu Ala Tyr Lys Lys Leu Met Thr Val Leu Lys Thr Tyr
705                 710                 715                 720
Leu Asp Thr Ser Ser Arg Gly Glu Gln Cys Glu Pro Ile Leu Arg Thr
                725                 730                 735
Leu Lys Ala Leu Glu Tyr Val Phe Lys Phe Ile Val Arg Ser Arg Thr
            740                 745                 750
Leu Phe Ser Gln Leu Tyr Glu Gly Lys Glu Gln Met Glu Phe Glu Glu
        755                 760                 765
Ser Met Arg Arg Leu Phe Glu Ser Ile Asn Asn Leu Met Lys Ser Gln
    770                 775                 780
Tyr Lys Thr Thr Ile Leu Leu Gln Val Ala Ala Leu Lys Tyr Ile Pro
785                 790                 795                 800
Ser Val Leu His Asp Val Glu Met Val Phe Asp Ala Lys Leu Leu Ser
                805                 810                 815
Gln Leu Leu Tyr Glu Phe Tyr Thr Cys Ile Pro Pro Val Lys Leu Gln
```

```
                   820             825             830
Lys Gln Lys Val Gln Ser Met Asn Glu Ile Val Gln Ser Asn Leu Phe
            835             840             845
Lys Lys Gln Glu Cys Arg Asp Ile Leu Leu Pro Val Ile Thr Lys Glu
850             855             860
Leu Lys Glu Leu Leu Glu Gln Lys Asp Asp Met Gln His Gln Val Leu
865             870             875             880
Glu Arg Lys Tyr Cys Val Glu Leu Leu Asn Ser Ile Leu Glu Val Leu
                885             890             895
Ser Tyr Gln Asp Ala Ala Phe Thr Tyr His His Ile Gln Glu Ile Met
            900             905             910
Val Gln Leu Leu Arg Thr Val Asn Arg Thr Val Ile Thr Met Gly Arg
            915             920             925
Asp His Ile Leu Ile Ser His Phe Val Ala Cys Met Thr Ala Ile Leu
            930             935             940
Asn Gln Met Gly Asp Gln His Tyr Ser Phe Tyr Ile Glu Thr Phe Gln
945             950             955             960
Thr Ser Ser Glu Leu Val Asp Phe Leu Met Glu Thr Phe Ile Met Phe
            965             970             975
Lys Asp Leu Ile Gly Lys Asn Val Tyr Pro Gly Asp Trp Met Ala Met
            980             985             990
Ser Met Val Gln Asn Arg Val Phe Leu Arg Ala Ile Asn Lys Phe Ala
        995             1000            1005
Glu Thr Met Asn Gln Lys Phe Leu Glu His Thr Asn Phe Glu Phe Gln
    1010            1015            1020
Leu Trp Asn Asn Tyr Phe His Leu Ala Val Ala Phe Ile Thr Gln Asp
1025            1030            1035            1040
Ser Leu Gln Leu Glu Gln Phe Ser His Ala Lys Tyr Asn Lys Ile Leu
            1045            1050            1055
Asn Lys Tyr Gly Asp Met Arg Arg Leu Ile Gly Phe Ser Ile Arg Asp
            1060            1065            1070
Met Trp Tyr Lys Leu Gly Gln Asn Lys Ile Cys Phe Ile Pro Gly Met
        1075            1080            1085
Val Gly Pro Ile Leu Glu Met Thr Leu Ile Pro Glu Ala Glu Leu Arg
        1090            1095            1100
Lys Ala Thr Ile Pro Ile Phe Phe Asp Met Met Leu Cys Glu Tyr Gln
1105            1110            1115            1120
Arg Ser Gly Asp Phe Lys Lys Phe Glu Asn Glu Ile Ile Leu Lys Leu
            1125            1130            1135
Asp His Glu Val Glu Gly Gly Arg Gly Asp Glu Gln Tyr Met Gln Leu
        1140            1145            1150
Leu Glu Ser Ile Leu Met Glu Cys Ala Ala Glu His Pro Thr Ile Ala
            1155            1160            1165
Lys Ser Val Glu Asn Phe Val Asn Leu Val Lys Gly Leu Leu Glu Lys
        1170            1175            1180
Leu Leu Asp Tyr Arg Gly Val Met Thr Asp Glu Ser Lys Asp Asn Arg
1185            1190            1195            1200
Met Ser Cys Thr Val Asn Leu Leu Asn Phe Tyr Lys Asp Asn Asn Arg
            1205            1210            1215
Glu Glu Met Tyr Ile Arg Tyr Leu Tyr Lys Leu Arg Asp Leu His Leu
        1220            1225            1230
Asp Cys Asp Asn Tyr Thr Glu Ala Ala Tyr Thr Leu Leu Leu His Thr
            1235            1240            1245
```

-continued

```
Trp Leu Leu Lys Trp Ser Asp Glu Gln Cys Ala Ser Gln Val Met Gln
    1250                1255                1260

Thr Gly Gln Gln His Pro Gln Thr His Arg Gln Leu Lys Glu Thr Leu
1265                1270                1275                1280

Tyr Glu Thr Ile Ile Gly Tyr Phe Asp Lys Gly Lys Met Trp Glu Glu
                1285                1290                1295

Ala Ile Ser Leu Cys Lys Glu Leu Ala Glu Gln Tyr Glu Met Glu Ile
            1300                1305                1310

Phe Asp Tyr Glu Leu Leu Ser Gln Asn Leu Ile Gln Gln Ala Lys Phe
        1315                1320                1325

Tyr Glu Ser Ile Met Lys Ile Leu Arg Pro Lys Pro Asp Tyr Phe Ala
    1330                1335                1340

Val Gly Tyr Tyr Gly Gln Gly Phe Pro Ser Phe Leu Arg Asn Lys Val
1345                1350                1355                1360

Phe Ile Tyr Arg Gly Lys Glu Tyr Glu Arg Arg Glu Asp Phe Gln Met
                1365                1370                1375

Gln Leu Met Thr Gln Phe Pro Asn Ala Glu Lys Met Asn Thr Thr Ser
            1380                1385                1390

Ala Pro Gly Asp Asp Val Lys Asn Ala Pro Gly Gln Tyr Ile Gln Cys
        1395                1400                1405

Phe Thr Val Gln Pro Val Leu Asp Glu His Pro Arg Phe Lys Asn Lys
    1410                1415                1420

Pro Val Pro Asp Gln Ile Ile Asn Phe Tyr Lys Ser Asn Tyr Val Gln
1425                1430                1435                1440

Arg Phe His Tyr Ser Arg Pro Val Arg Arg Gly Thr Val Asp Pro Glu
                1445                1450                1455

Asn Glu Phe Ala Ser Met Trp Ile Glu Arg Thr Ser Phe Val Thr Ala
            1460                1465                1470

Tyr Lys Leu Pro Gly Ile Leu Arg Trp Phe Glu Val Val His Met Ser
        1475                1480                1485

Gln Thr Thr Ile Ser Pro Leu Glu Asn Ala Ile Glu Thr Met Ser Thr
    1490                1495                1500

Ala Asn Glu Lys Ile Leu Met Met Ile Asn Gln Tyr Gln Ser Asp Glu
1505                1510                1515                1520

Thr Leu Pro Ile Asn Pro Leu Ser Met Leu Leu Asn Gly Ile Val Asp
                1525                1530                1535

Pro Ala Val Met Gly Gly Phe Ala Lys Tyr Glu Lys Ala Phe Phe Thr
            1540                1545                1550

Glu Glu Tyr Val Arg Asp His Pro Glu Asp Gln Asp Lys Leu Thr His
        1555                1560                1565

Leu Lys Asp Leu Ile Ala Trp Gln Ile Pro Phe Leu Gly Ala Gly Ile
    1570                1575                1580

Lys Ile His Glu Lys Arg Val Ser Asp Asn Leu Arg Pro Phe His Asp
1585                1590                1595                1600

Arg Met Glu Glu Cys Phe Lys Asn Leu Lys Met Lys Val Glu Lys Glu
                1605                1610                1615

Tyr Gly Val Arg Glu Met Pro Asp Phe Asp Asp Arg Arg Val Gly Arg
            1620                1625                1630

Pro Arg Ser Met Leu Arg Ser Tyr Arg Gln Met Ser Ile Ile Ser Leu
        1635                1640                1645

Ala Ser Met Asn Ser Asp Cys Ser Thr Pro Ser Lys Pro Thr Ser Glu
    1650                1655                1660
```

```
Ser Phe Asp Leu Glu Leu Ala Ser Pro Lys Thr Pro Arg Val Glu Gln
1665                1670                1675                1680

Glu Glu Pro Ile Ser Pro Gly Ser Thr Leu Pro Glu Val Lys Leu Arg
            1685                1690                1695

Arg Ser Lys Lys Arg Thr Lys Arg Ser Ser Val Val Phe Ala Asp Glu
        1700                1705                1710

Lys Ala Ala Ala Glu Ser Asp Leu Lys Arg Leu Ser Arg Lys His Glu
    1715                1720                1725

Phe Met Ser Asp Thr Asn Leu Ser Glu His Ala Ala Ile Pro Leu Lys
1730                1735                1740

Ala Ser Val Leu Ser Gln Met Ser Phe Ala Ser Gln Ser Met Pro Thr
1745                1750                1755                1760

Ile Pro Ala Leu Ala Leu Ser Val Ala Gly Ile Pro Gly Leu Asp Glu
            1765                1770                1775

Ala Asn Thr Ser Pro Arg Leu Ser Gln Thr Phe Leu Gln Leu Ser Asp
        1780                1785                1790

Gly Asp Lys Lys Thr Leu Thr Arg Lys Lys Val Asn Gln Phe Phe Lys
    1795                1800                1805

Thr Met Leu Ala Ser Lys Ser Ala Glu Glu Gly Lys Gln Ile Pro Asp
1810                1815                1820

Ser Leu Ser Thr Asp Leu
1825                1830

<210> SEQ ID NO 3
<211> LENGTH: 727
<212> TYPE: PRT
<213> ORGANISM: Mus musculus

<400> SEQUENCE: 3

Met Pro Pro Pro Ser Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
            20                  25                  30

Ile Ile Lys Glu Val Cys Asp Gly Trp Ser Leu Ala Asn His Glu Tyr
        35                  40                  45

Phe Ala Leu Gln His Ala Asp Ser Ser Asn Phe Tyr Ile Thr Glu Lys
    50                  55                  60

Asn Arg Asn Glu Ile Lys Asn Gly Thr Ile Leu Arg Leu Thr Thr Ser
65                  70                  75                  80

Pro Ala Gln Asn Ala Gln Gln Leu His Glu Arg Ile Gln Ser Ser Ser
                85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
        115                 120                 125

Leu Thr Gln Met Val Glu Ser Gly Thr Glu Arg Tyr Gln Lys Leu Gln
    130                 135                 140

Lys Ile Met Lys Pro Cys Phe Gly Asp Met Leu Ser Phe Thr Leu Thr
145                 150                 155                 160

Ala Phe Val Glu Leu Met Asp His Gly Ile Val Ser Trp Asp Thr Phe
                165                 170                 175

Ser Val Ala Phe Ile Lys Lys Ile Ala Ser Phe Val Asn Lys Ser Ala
            180                 185                 190

Ile Asp Ile Ser Ile Leu Gln Arg Ser Leu Ala Ile Leu Glu Ser Met
        195                 200                 205
```

```
Val Leu Asn Ser His Asp Leu Tyr Gln Lys Val Ala Gln Glu Ile Thr
    210                 215                 220
Ile Gly Gln Leu Ile Pro His Leu Gln Gly Thr Asp Gln Glu Ile Gln
225                 230                 235                 240
Thr Tyr Thr Ile Ala Val Ile Asn Ala Leu Phe Leu Lys Ala Pro Asp
                245                 250                 255
Glu Arg Arg Gln Glu Met Ala Asn Ile Leu Ala Gln Lys Gln Leu Arg
            260                 265                 270
Tyr Ile Ile Leu Thr His Val Ile Arg Ala Gln Arg Ala Ile Asn Asn
        275                 280                 285
Glu Met Ala His Gln Leu Tyr Val Leu Gln Val Leu Thr Phe Asn Leu
    290                 295                 300
Leu Glu Asp Arg Met Met Thr Lys Met Asp Pro Gln Asp Gln Ala Gln
305                 310                 315                 320
Arg Asp Ile Ile Phe Glu Leu Arg Arg Ile Ala Phe Asp Ala Glu Ser
                325                 330                 335
Glu Pro Asn Asn Ser Ser Gly Ser Met Glu Lys Arg Lys Ser Met Tyr
            340                 345                 350
Thr Arg Asp Tyr Lys Lys Leu Gly Phe Ile Asn His Val Asn Pro Ala
        355                 360                 365
Met Asp Phe Thr Gln Thr Pro Pro Gly Met Leu Ala Leu Asp Asn Met
    370                 375                 380
Leu Tyr Phe Ala Lys His His Gln Asp Ala Tyr Ile Arg Ile Val Leu
385                 390                 395                 400
Glu Asn Ser Ser Arg Glu Asp Lys His Glu Cys Pro Phe Gly Arg Ser
                405                 410                 415
Ser Ile Glu Leu Thr Lys Met Leu Cys Glu Ile Leu Lys Val Gly Glu
            420                 425                 430
Leu Pro Ser Glu Thr Cys Asn Asp Phe His Pro Met Phe Phe Thr His
        435                 440                 445
Asp Arg Ser Phe Glu Glu Phe Phe Cys Ile Cys Ile Gln Leu Leu Asn
    450                 455                 460
Lys Thr Trp Lys Glu Met Arg Ala Thr Ser Glu Asp Phe Asn Lys Val
465                 470                 475                 480
Met Gln Val Val Lys Glu Gln Val Met Arg Ala Leu Thr Thr Lys Pro
                485                 490                 495
Ser Ser Leu Asp Gln Phe Lys Ser Lys Leu Gln Asn Leu Ser Tyr Thr
            500                 505                 510
Glu Ile Leu Lys Ile Arg Gln Ser Glu Arg Met Asn Gln Glu Asp Phe
        515                 520                 525
Gln Ser Arg Pro Ile Leu Glu Leu Lys Glu Lys Ile Gln Pro Glu Ile
    530                 535                 540
Leu Glu Leu Ile Lys Gln Gln Arg Leu Asn Arg Leu Val Glu Gly Thr
545                 550                 555                 560
Cys Phe Arg Lys Leu Asn Ala Arg Arg Arg Gln Asp Lys Phe Trp Tyr
                565                 570                 575
Cys Arg Leu Ser Pro Asn His Lys Val Leu His Tyr Gly Asp Leu Glu
            580                 585                 590
Glu Ser Pro Gln Gly Glu Val Pro His Asp Ser Leu Gln Asp Lys Leu
        595                 600                 605
Pro Val Ala Asp Ile Lys Ala Val Val Thr Gly Lys Asp Cys Pro His
    610                 615                 620
```

```
Met Lys Glu Lys Gly Ala Leu Lys Gln Asn Lys Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
            660                 665                 670

Leu Gly Lys Asp Met Met Ser Asp Leu Thr Arg Asn Asp Leu Asp Thr
        675                 680                 685

Leu Leu Ser Met Glu Ile Lys Leu Arg Leu Leu Asp Leu Glu Asn Ile
    690                 695                 700

Gln Ile Pro Asp Ala Pro Pro Ile Pro Lys Glu Pro Ser Asn Tyr
705                 710                 715                 720

Asp Phe Val Tyr Asp Cys Asn
                725
```

<210> SEQ ID NO 4
<211> LENGTH: 727
<212> TYPE: PRT
<213> ORGANISM: Homo sapiens

<400> SEQUENCE: 4

```
Met Pro Pro Pro Ala Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
                20                  25                  30

Ile Ile Lys Glu Val Cys Asp Gly Trp Ser Leu Ala Asn His Glu Tyr
            35                  40                  45

Phe Ala Leu Gln His Ala Asp Ser Ser Asn Phe Tyr Ile Thr Glu Lys
        50                  55                  60

Asn Arg Asn Glu Ile Lys Asn Gly Thr Ile Leu Arg Leu Thr Thr Ser
65                  70                  75                  80

Pro Ala Gln Asn Ala Gln Gln Leu His Glu Arg Ile Gln Ser Ser Ser
                85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
        115                 120                 125

Leu Thr Gln Met Val Glu Ser Gly Thr Glu Arg Tyr Gln Lys Leu Gln
130                 135                 140

Lys Ile Met Lys Pro Cys Phe Gly Asp Met Leu Ser Phe Thr Leu Thr
145                 150                 155                 160

Ala Phe Val Glu Leu Met Asp His Gly Ile Val Ser Trp Asp Thr Phe
                165                 170                 175

Ser Val Ala Phe Ile Lys Lys Ile Ala Ser Phe Val Asn Lys Ser Ala
            180                 185                 190

Ile Asp Ile Ser Ile Leu Gln Arg Ser Leu Ala Ile Leu Glu Ser Met
        195                 200                 205

Val Leu Asn Ser His Asp Leu Tyr Gln Lys Val Ala Gln Glu Ile Thr
    210                 215                 220

Ile Gly Gln Leu Ile Pro His Leu Gln Gly Ser Asp Gln Glu Ile Gln
225                 230                 235                 240

Thr Tyr Thr Ile Ala Val Ile Asn Ala Leu Phe Leu Lys Ala Pro Asp
                245                 250                 255

Glu Arg Arg Gln Glu Met Ala Asn Ile Leu Ala Gln Lys Gln Leu Arg
            260                 265                 270
```

-continued

```
Ser Ile Ile Leu Thr His Val Ile Arg Ala Gln Arg Ala Ile Asn Asn
            275                 280                 285

Glu Met Ala His Gln Leu Tyr Val Leu Gln Val Leu Thr Phe Asn Leu
        290                 295                 300

Leu Glu Asp Arg Met Met Thr Lys Met Asp Pro Gln Asp Gln Ala Gln
305                 310                 315                 320

Arg Asp Ile Ile Phe Glu Leu Arg Arg Ile Ala Phe Asp Ala Glu Ser
                325                 330                 335

Glu Pro Asn Asn Ser Ser Gly Ser Met Glu Lys Arg Lys Ser Met Tyr
            340                 345                 350

Thr Arg Asp Tyr Lys Lys Leu Gly Phe Ile Asn His Val Asn Pro Ala
        355                 360                 365

Met Asp Phe Thr Gln Thr Pro Pro Gly Met Leu Ala Leu Asp Asn Met
    370                 375                 380

Leu Tyr Phe Ala Lys His His Gln Asp Ala Tyr Ile Arg Ile Val Leu
385                 390                 395                 400

Glu Asn Ser Ser Arg Glu Asp Lys His Glu Cys Pro Phe Gly Arg Ser
                405                 410                 415

Ser Ile Glu Leu Thr Lys Met Leu Cys Glu Ile Leu Lys Val Gly Glu
            420                 425                 430

Leu Pro Ser Glu Thr Cys Asn Asp Phe His Pro Met Phe Phe Thr His
        435                 440                 445

Asp Arg Ser Phe Glu Glu Phe Phe Cys Ile Cys Ile Gln Leu Leu Asn
    450                 455                 460

Lys Thr Trp Lys Glu Met Arg Ala Thr Ser Glu Asp Phe Asn Lys Val
465                 470                 475                 480

Met Gln Val Val Lys Glu Gln Val Met Arg Ala Leu Thr Thr Lys Pro
                485                 490                 495

Ser Ser Leu Asp Gln Phe Lys Ser Lys Leu Gln Asn Leu Ser Tyr Thr
            500                 505                 510

Glu Ile Leu Lys Ile Arg Gln Ser Glu Arg Met Asn Gln Glu Asp Phe
        515                 520                 525

Gln Ser Arg Pro Ile Leu Glu Leu Lys Glu Lys Ile Gln Pro Glu Ile
    530                 535                 540

Leu Glu Leu Ile Lys Gln Arg Leu Asn Arg Leu Val Glu Gly Thr
545                 550                 555                 560

Cys Phe Arg Lys Leu Asn Ala Arg Arg Gln Asp Lys Phe Trp Tyr
                565                 570                 575

Cys Arg Leu Ser Pro Asn His Lys Val Leu His Tyr Gly Asp Leu Glu
            580                 585                 590

Glu Ser Pro Gln Gly Glu Val Pro His Asp Ser Leu Gln Asp Lys Leu
        595                 600                 605

Pro Val Ala Asp Ile Lys Ala Val Val Thr Gly Lys Asp Cys Pro His
    610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
            660                 665                 670

Leu Gly Lys Asp Met Met Ser Asp Leu Thr Arg Asn Asp Leu Asp Thr
        675                 680                 685
```

```
Leu Leu Ser Met Glu Ile Lys Leu Arg Leu Leu Asp Leu Glu Asn Ile
    690             695                 700
Gln Ile Pro Asp Ala Pro Pro Ile Pro Lys Glu Pro Ser Asn Tyr
705             710                 715                 720
Asp Phe Val Tyr Asp Cys Asn
            725
```

<210> SEQ ID NO 5
<211> LENGTH: 1591
<212> TYPE: PRT
<213> ORGANISM: Mus musculus

<400> SEQUENCE: 5

```
Met Gly Asn Ala Glu Ser Gln Asn Val Asp His Glu Phe Tyr Gly Glu
  1               5                  10                  15
Lys His Ala Ser Leu Gly Arg Lys His Thr Ser Arg Ser Leu Arg Leu
                 20                  25                  30
Ser His Lys Thr Arg Arg Thr His Ala Ser Ser Gly Lys Ala Ile
             35                  40                  45
His Arg Asn Ser Glu Val Ser Thr Arg Ser Ser Thr Pro Ser Ile
         50                  55                  60
Pro Gln Ser Leu Ala Glu Asn Gly Leu Glu Pro Phe Ser Gln Glu Gly
 65                  70                  75                  80
Ala Leu Asp Asp Phe Gly Asp Pro Ile Trp Val Asp Arg Val Asp Met
                 85                  90                  95
Gly Leu Arg Pro Val Ser Tyr Thr Asp Ser Ser Val Thr Pro Ser Val
                100                 105                 110
Asp Gly Ser Ile Val Leu Thr Ala Ala Ser Val Gln Ser Met Pro Asp
                115                 120                 125
Ser Glu Glu Ser Arg Leu Tyr Gly Asp Asp Ala Thr Tyr Leu Ala Glu
130                 135                 140
Gly Gly Arg Arg Gln Cys Pro Tyr Thr Ser Asn Gly Pro Thr Phe Met
145                 150                 155                 160
Glu Thr Ala Ser Phe Lys Lys Lys Arg Ser Lys Ser Ala Asp Ile Trp
                165                 170                 175
Arg Glu Asp Ser Leu Glu Phe Ser Leu Ser Asp Leu Ser Gln Glu His
                180                 185                 190
Leu Thr Ser Asn Glu Glu Ile Leu Gly Ser Ala Glu Glu Lys Asp Cys
            195                 200                 205
Glu Glu Ala Arg Gly Met Glu Thr Glu Ala Ser Pro Arg Gln Leu Ser
210                 215                 220
Thr Cys Gln Arg Ala Asn Ser Leu Gly Asp Leu Tyr Ala Gln Lys Asn
225                 230                 235                 240
Ser Gly Val Lys Ala Asn Gly Gly Pro Arg Asn Arg Phe Ser Ser Tyr
                245                 250                 255
Cys Arg Asn Leu Val Ser Asp Ile Pro Asp Leu Ala Lys His Lys Met
                260                 265                 270
Pro Pro Ala Ala Ala Glu Glu Thr Pro Pro Tyr Ser Asn Tyr Asn Thr
            275                 280                 285
Leu Pro Cys Arg Lys Ser His Cys Leu Ser Glu Gly Ala Thr Asn Pro
        290                 295                 300
Gln Ile Ser Leu Ser Lys Ser Met Gln Gly Arg Arg Ala Lys Thr Thr
305                 310                 315                 320
Gln Asp Val Asn Thr Gly Glu Gly Ser Glu Phe Ala Asp Ser Gly Ile
                325                 330                 335
```

```
Glu Gly Ala Thr Thr Asp Thr Asp Leu Leu Ser Arg Arg Ser Asn Ala
            340                 345                 350

Thr Asn Ser Ser Tyr Ser Pro Pro Thr Gly Arg Ala Phe Val Gly Ser
        355                 360                 365

Asp Ser Gly Ser Ser Ser Thr Gly Asp Arg Ala Arg Gln Gly Val Tyr
    370                 375                 380

Glu Asn Phe Arg Arg Glu Leu Glu Met Ser Thr Thr Asn Ser Glu Ser
385                 390                 395                 400

Leu Glu Glu Ala Gly Ser Ala His Ser Asp Glu Gln Ser Ser Gly Thr
                405                 410                 415

Leu Ser Ser Pro Gly Gln Ser Asp Ile Leu Leu Thr Ala Ala Gln Gly
            420                 425                 430

Thr Val Arg Lys Ala Gly Ala Leu Ala Val Lys Asn Phe Leu Val His
        435                 440                 445

Lys Lys Asn Lys Lys Val Glu Ser Ala Thr Arg Arg Lys Trp Lys His
450                 455                 460

Tyr Trp Val Ser Leu Lys Gly Cys Thr Leu Phe Phe Tyr Glu Thr Asp
465                 470                 475                 480

Gly Arg Ser Gly Ile Asp His Asn Ser Val Pro Lys His Ala Val Trp
                485                 490                 495

Val Glu Asn Ser Ile Val Gln Ala Val Pro Glu His Pro Lys Lys Asp
            500                 505                 510

Phe Val Phe Cys Leu Ser Asn Ser Leu Gly Asp Ala Phe Leu Phe Gln
        515                 520                 525

Thr Thr Ser Gln Thr Glu Leu Glu Asn Trp Ile Thr Ala Ile His Ser
    530                 535                 540

Ala Cys Ala Ala Ala Val Ala Arg His His His Lys Glu Asp Thr Leu
545                 550                 555                 560

Arg Leu Leu Lys Ser Glu Ile Lys Lys Leu Glu Gln Lys Ile Asp Met
                565                 570                 575

Asp Glu Lys Met Lys Lys Met Gly Glu Met Gln Leu Ser Ser Val Thr
            580                 585                 590

Asp Ser Lys Lys Lys Lys Thr Ile Leu Asp Gln Ile Phe Val Trp Glu
        595                 600                 605

Gln Asn Leu Glu Gln Phe Gln Met Asp Leu Phe Arg Phe Arg Cys Tyr
    610                 615                 620

Leu Ala Ser Leu Gln Gly Gly Glu Leu Pro Asn Pro Lys Arg Leu Leu
625                 630                 635                 640

Ala Phe Ala Ser Arg Pro Thr Lys Val Ala Met Gly Arg Leu Gly Ile
                645                 650                 655

Phe Ser Val Ser Ser Phe His Ala Leu Val Ala Ala Arg Thr Gly Glu
            660                 665                 670

Ile Gly Val Arg Arg Arg Thr Gln Ala Met Ser Arg Ser Ala Ser Lys
        675                 680                 685

Arg Arg Ser Arg Phe Ser Ser Leu Trp Gly Leu Asp Thr Thr Ser Lys
    690                 695                 700

Lys Lys Gln Gly Arg Pro Thr Ile Asn Gln Val Phe Gly Glu Gly Thr
705                 710                 715                 720

Asp Ala Val Lys Arg Ser Leu Glu Gly Ile Phe Asp Asp Thr Val Pro
                725                 730                 735

Asp Gly Lys Arg Glu Lys Glu Val Val Leu Pro Ser Val His Gln His
            740                 745                 750
```

-continued

```
Asn Pro Asp Cys Asp Ile Trp Val His Glu Tyr Phe Thr Pro Ser Trp
        755                 760                 765
Phe Cys Leu Pro Asn Asn Gln Pro Ala Leu Thr Val Val Arg Pro Gly
770                 775                 780
Asp Thr Ala Arg Asp Thr Leu Glu Leu Ile Cys Lys Thr His Gln Leu
785                 790                 795                 800
Asp His Ser Ala His Tyr Leu Arg Leu Lys Phe Leu Met Glu Asn Arg
                805                 810                 815
Val Gln Phe Tyr Ile Pro Gln Pro Glu Glu Asp Ile Tyr Glu Leu Leu
            820                 825                 830
Tyr Lys Glu Ile Glu Ile Cys Pro Lys Val Thr Gln Asn Ile His Ile
        835                 840                 845
Glu Lys Ser Asp Ala Ala Asp Asn Tyr Gly Phe Leu Leu Ser Ser
850                 855                 860
Val Asp Glu Asp Gly Ile Arg Arg Leu Tyr Val Asn Ser Val Lys Glu
865                 870                 875                 880
Thr Gly Leu Ala Ser Lys Lys Gly Leu Lys Ala Gly Asp Glu Ile Leu
                885                 890                 895
Glu Ile Asn Asn Arg Ala Ala Gly Thr Leu Asn Ser Ser Met Leu Lys
            900                 905                 910
Asp Phe Leu Ser Gln Pro Ser Leu Gly Leu Leu Val Arg Thr Tyr Pro
        915                 920                 925
Glu Pro Glu Gly Gly Val Glu Leu Leu Glu Asn Pro Pro His Arg Val
    930                 935                 940
Asp Gly Pro Val Asp Leu Gly Glu Ser Pro Leu Ala Phe Leu Thr Ser
945                 950                 955                 960
Asn Pro Gly His Ser Leu Ser Ser Glu Gln Gly Ser Ser Ala Glu Thr
                965                 970                 975
Ala Pro Glu Glu Gly Glu Gly Pro Asp Leu Glu Ser Ser Asp Glu Thr
            980                 985                 990
Asp His Ser Ser Lys Ser Thr Glu Gln Val Ala Ala Phe Cys Arg Ser
        995                 1000                1005
Leu His Glu Met Ser Pro Ser Asp Ser Ser Pro Ser Pro Gln Asp Ala
    1010                1015                1020
Thr Ser Pro Gln Leu Ala Thr Thr Arg Gln Leu Ser Asp Ala Asp Lys
1025                1030                1035                1040
Leu Arg Lys Val Ile Cys Glu Leu Leu Glu Thr Glu Arg Thr Tyr Val
                1045                1050                1055
Lys Asp Leu Asn Cys Leu Met Glu Arg Tyr Leu Lys Pro Leu Gln Lys
            1060                1065                1070
Glu Thr Phe Leu Thr Gln Asp Glu Leu Asp Val Leu Phe Gly Asn Leu
        1075                1080                1085
Thr Glu Met Val Glu Phe Gln Val Glu Phe Leu Lys Thr Leu Glu Asp
    1090                1095                1100
Gly Val Arg Leu Val Pro Asp Leu Glu Lys Leu Glu Lys Val Asp Gln
1105                1110                1115                1120
Phe Lys Lys Val Leu Phe Ser Leu Gly Gly Ser Phe Leu Tyr Tyr Ala
                1125                1130                1135
Asp Arg Phe Lys Leu Tyr Ser Ala Phe Cys Ala Ser His Thr Lys Val
            1140                1145                1150
Pro Lys Val Leu Val Lys Ala Lys Thr Asp Thr Ala Phe Lys Ala Phe
        1155                1160                1165
Leu Asp Ala Gln Asn Pro Arg Gln Gln His Ser Ser Thr Leu Glu Ser
```

-continued

```
            1170                1175                1180
Tyr Leu Ile Lys Pro Ile Gln Arg Val Leu Lys Tyr Pro Leu Leu Leu
1185                1190                1195                1200

Arg Glu Leu Phe Ala Leu Thr Asp Ala Glu Ser Glu His Tyr His
                1205                1210                1215

Leu Asp Val Ala Ile Lys Thr Met Asn Lys Val Ala Ser His Ile Asn
            1220                1225                1230

Glu Met Gln Lys Ile His Glu Glu Phe Gly Ala Val Phe Asp Gln Leu
        1235                1240                1245

Ile Ala Glu Gln Thr Gly Glu Lys Lys Glu Val Ala Asp Leu Ser Met
    1250                1255                1260

Gly Asp Leu Leu His Thr Ser Val Ile Trp Leu Asn Pro Pro Ala
1265                1270                1275                1280

Ser Leu Gly Lys Trp Lys Lys Glu Pro Glu Leu Ala Ala Phe Val Phe
                1285                1290                1295

Lys Thr Ala Val Val Leu Val Tyr Lys Asp Gly Ser Lys Gln Lys Lys
            1300                1305                1310

Lys Leu Val Gly Ser His Arg Leu Ser Ile Tyr Glu Glu Trp Asp Pro
        1315                1320                1325

Phe Arg Phe Arg His Met Ile Pro Thr Glu Ala Leu Gln Val Arg Ala
    1330                1335                1340

Leu Pro Ser Ala Asp Ala Glu Ala Asn Ala Val Cys Glu Ile Val His
1345                1350                1355                1360

Val Lys Ser Glu Ser Glu Gly Arg Pro Glu Arg Val Phe His Leu Cys
            1365                1370                1375

Cys Ser Ser Pro Glu Ser Arg Lys Asp Phe Leu Lys Ser Val His Ser
        1380                1385                1390

Ile Leu Arg Asp Lys His Arg Arg Gln Leu Leu Lys Thr Glu Ser Leu
    1395                1400                1405

Pro Ser Ala Gln Gln Tyr Val Pro Phe Gly Gly Lys Arg Leu Cys Ala
    1410                1415                1420

Leu Lys Gly Ala Arg Pro Ala Met Ser Arg Ala Val Ser Ala Pro Ser
1425                1430                1435                1440

Lys Ser Leu Gly Arg Arg Arg Arg Leu Ala Arg Asn Arg Phe Thr
                1445                1450                1455

Ile Asp Ser Asp Ala Ile Ser Ala Ser Ser Pro Glu Lys Glu Pro Gln
            1460                1465                1470

Gln Pro Ala Gly Gly Gly Asp Thr Asp Arg Trp Val Glu Glu Gln Phe
        1475                1480                1485

Asp Leu Ala Gln Tyr Glu Glu Gln Asp Asp Ile Lys Glu Thr Asp Ile
    1490                1495                1500

Leu Ser Asp Asp Asp Glu Phe Cys Glu Ser Leu Lys Gly Ala Ser Val
1505                1510                1515                1520

Asp Arg Asp Leu Gln Glu Gln Leu Gln Ala Ala Ser Ile Ser Gln Arg
            1525                1530                1535

Ala Arg Gly Arg Arg Thr Leu Asp Ser His Ala Ser Arg Met Thr Gln
        1540                1545                1550

Leu Lys Lys Gln Ala Ala Leu Ser Gly Ile Asn Gly Gly Leu Glu Ser
    1555                1560                1565

Ala Ser Glu Glu Val Ile Trp Val Arg Arg Glu Asp Phe Ala Pro Ser
    1570                1575                1580

Arg Lys Leu Asn Thr Glu Ile
1585                1590
```

<210> SEQ ID NO 6
<211> LENGTH: 1591
<212> TYPE: PRT
<213> ORGANISM: Homo sapiens

<400> SEQUENCE: 6

```
Met Gly Asn Ala Glu Ser Gln His Val Glu His Glu Phe Tyr Gly Glu
  1               5                  10                  15

Lys His Ala Ser Leu Gly Arg Asn Asp Thr Ser Arg Ser Leu Arg Leu
             20                  25                  30

Ser His Lys Thr Arg Arg Thr Arg His Ala Ser Ser Gly Lys Val Ile
         35                  40                  45

His Arg Asn Ser Glu Val Ser Thr Arg Ser Ser Thr Pro Ser Ile
     50                  55                  60

Pro Gln Ser Leu Ala Glu Asn Gly Leu Glu Pro Phe Ser Gln Asp Gly
 65                  70                  75                  80

Thr Leu Glu Asp Phe Gly Ser Pro Ile Trp Val Asp Arg Val Asp Met
                 85                  90                  95

Gly Leu Arg Pro Val Ser Tyr Thr Asp Ser Ser Val Thr Pro Ser Val
            100                 105                 110

Asp Ser Ser Ile Val Leu Thr Ala Ala Ser Val Gln Ser Met Pro Asp
        115                 120                 125

Thr Glu Glu Ser Arg Leu Tyr Gly Asp Asp Ala Thr Tyr Leu Ala Glu
    130                 135                 140

Gly Gly Arg Arg Gln His Ser Tyr Thr Ser Asn Gly Pro Thr Phe Met
145                 150                 155                 160

Glu Thr Ala Ser Phe Lys Lys Lys Arg Ser Lys Ser Ala Asp Ile Trp
                165                 170                 175

Arg Glu Asp Ser Leu Glu Phe Ser Leu Ser Asp Leu Ser Gln Glu His
            180                 185                 190

Leu Thr Ser Asn Glu Glu Ile Leu Gly Ser Ala Glu Glu Lys Asp Cys
        195                 200                 205

Glu Glu Ala Arg Gly Met Glu Thr Arg Ala Ser Pro Arg Gln Leu Ser
    210                 215                 220

Thr Cys Gln Arg Ala Asn Ser Leu Gly Asp Leu Tyr Ala Gln Lys Asn
225                 230                 235                 240

Ser Gly Val Thr Ala Asn Met Gly Pro Gly Ser Lys Phe Ala Gly Tyr
                245                 250                 255

Cys Arg Asn Leu Val Ser Asp Ile Pro Asn Leu Ala Asn His Lys Met
            260                 265                 270

Pro Pro Ala Ala Ala Glu Glu Thr Pro Tyr Ser Asn Tyr Asn Thr
        275                 280                 285

Leu Pro Cys Arg Lys Ser His Cys Leu Ser Glu Gly Ala Thr Asn Pro
    290                 295                 300

Gln Ile Ser His Ser Asn Ser Met Gln Gly Arg Arg Ala Lys Thr Thr
305                 310                 315                 320

Gln Asp Val Asn Ala Gly Glu Gly Ser Glu Phe Ala Asp Ser Gly Ile
                325                 330                 335

Glu Gly Ala Thr Thr Asp Thr Asp Leu Leu Ser Arg Arg Ser Asn Ala
            340                 345                 350

Thr Asn Ser Ser Tyr Ser Pro Thr Thr Gly Arg Ala Phe Val Gly Ser
        355                 360                 365

Asp Ser Gly Ser Ser Ser Thr Gly Asp Ala Ala Arg Gln Gly Val Tyr
```

-continued

```
            370                 375                 380
Glu Asn Phe Arg Arg Glu Leu Glu Met Ser Thr Thr Asn Ser Glu Ser
385                 390                 395                 400

Leu Glu Glu Ala Gly Ser Ala His Ser Asp Glu Gln Ser Ser Gly Thr
                405                 410                 415

Leu Ser Ser Pro Gly Gln Ser Asp Ile Leu Thr Ala Ala Gln Gly
                420                 425                 430

Thr Val Arg Lys Ala Gly Ala Leu Ala Val Lys Asn Phe Leu Val His
        435                 440                 445

Lys Lys Asn Lys Lys Val Glu Ser Ala Thr Arg Arg Lys Trp Lys His
450                 455                 460

Tyr Trp Val Ser Leu Lys Gly Cys Thr Leu Phe Phe Tyr Glu Ser Asp
465                 470                 475                 480

Gly Arg Ser Gly Ile Asp His Asn Ser Ile Pro Lys His Ala Val Trp
                485                 490                 495

Val Glu Asn Ser Ile Val Gln Ala Val Pro Glu His Pro Lys Lys Asp
                500                 505                 510

Phe Val Phe Cys Leu Ser Asn Ser Leu Gly Asp Ala Phe Leu Phe Gln
            515                 520                 525

Thr Thr Ser Gln Thr Glu Leu Glu Asn Trp Ile Thr Ala Ile His Ser
530                 535                 540

Ala Cys Ala Thr Ala Val Ala Arg His His His Lys Glu Asp Thr Leu
545                 550                 555                 560

Arg Leu Leu Lys Ser Glu Ile Lys Lys Leu Glu Gln Lys Ile Asp Met
                565                 570                 575

Asp Glu Lys Met Lys Lys Met Gly Glu Met Gln Leu Ser Ser Val Thr
                580                 585                 590

Asp Ser Lys Lys Lys Lys Thr Ile Leu Asp Gln Ile Phe Val Trp Glu
        595                 600                 605

Gln Asn Leu Glu Gln Phe Gln Met Asp Leu Phe Arg Phe Arg Cys Tyr
                610                 615                 620

Leu Ala Ser Leu Gln Gly Gly Glu Leu Pro Asn Pro Lys Arg Leu Leu
625                 630                 635                 640

Ala Phe Ala Ser Arg Pro Thr Lys Val Ala Met Gly Arg Leu Gly Ile
                645                 650                 655

Phe Ser Val Ser Ser Phe His Ala Leu Val Ala Ala Arg Thr Gly Glu
                660                 665                 670

Thr Gly Val Arg Arg Arg Thr Gln Ala Met Ser Arg Ser Ala Ser Lys
        675                 680                 685

Arg Arg Ser Arg Phe Ser Ser Leu Trp Gly Leu Asp Thr Thr Ser Lys
690                 695                 700

Lys Lys Gln Gly Arg Pro Ser Ile Asn Gln Val Phe Gly Glu Gly Thr
705                 710                 715                 720

Glu Ala Val Lys Lys Ser Leu Glu Gly Ile Phe Asp Asp Ile Val Pro
                725                 730                 735

Asp Gly Lys Arg Glu Lys Glu Val Val Leu Pro Asn Val His Gln His
                740                 745                 750

Asn Pro Asp Cys Asp Ile Trp Val His Glu Tyr Phe Thr Pro Ser Trp
            755                 760                 765

Phe Cys Leu Pro Asn Asn Gln Pro Ala Leu Thr Val Val Arg Pro Gly
        770                 775                 780

Asp Thr Ala Arg Asp Thr Leu Glu Leu Ile Cys Lys Thr His Gln Leu
785                 790                 795                 800
```

-continued

```
Asp His Ser Ala His Tyr Leu Arg Leu Lys Phe Leu Ile Glu Asn Lys
                805                 810                 815

Met Gln Leu Tyr Val Pro Gln Pro Glu Glu Asp Ile Tyr Glu Leu Leu
            820                 825                 830

Tyr Lys Glu Ile Glu Ile Cys Pro Lys Val Thr His Ser Ile His Ile
        835                 840                 845

Glu Lys Ser Asp Thr Ala Ala Asp Thr Tyr Gly Phe Ser Leu Ser Ser
    850                 855                 860

Val Glu Glu Asp Gly Ile Arg Arg Leu Tyr Val Asn Ser Val Lys Glu
865                 870                 875                 880

Thr Gly Leu Ala Ser Lys Lys Gly Leu Lys Ala Gly Asp Glu Ile Leu
                885                 890                 895

Glu Ile Asn Asn Arg Ala Ala Asp Ala Leu Asn Ser Ser Met Leu Lys
            900                 905                 910

Asp Phe Leu Ser Gln Pro Ser Leu Gly Leu Leu Val Arg Thr Tyr Pro
        915                 920                 925

Glu Leu Glu Glu Gly Val Glu Leu Leu Glu Ser Pro His Arg Val
    930                 935                 940

Asp Gly Pro Ala Asp Leu Asp Glu Ser Pro Leu Ala Phe Leu Thr Ser
945                 950                 955                 960

Asn Pro Gly His Ser Leu Cys Ser Glu Gln Gly Ser Ser Ala Glu Thr
                965                 970                 975

Ala Pro Glu Glu Thr Glu Gly Pro Asp Leu Glu Ser Ser Asp Glu Thr
            980                 985                 990

Asp His Ser Ser Lys Ser Thr Glu Gln Val Ala Ala Phe Cys Arg Ser
        995                 1000                1005

Leu His Glu Met Asn Pro Ser Asp Gln Asn Pro Ser Pro Gln Asp Ser
    1010                1015                1020

Thr Gly Pro Gln Leu Ala Thr Met Arg Gln Leu Ser Asp Ala Asp Asn
1025                1030                1035                1040

Val Arg Lys Val Ile Cys Glu Leu Leu Glu Thr Glu Arg Thr Tyr Val
                1045                1050                1055

Lys Asp Leu Asn Cys Leu Met Glu Arg Tyr Leu Lys Pro Leu Gln Lys
            1060                1065                1070

Glu Thr Phe Leu Thr Gln Asp Glu Leu Asp Val Leu Phe Gly Asn Leu
        1075                1080                1085

Thr Glu Met Val Glu Phe Gln Val Glu Phe Leu Lys Thr Leu Glu Asp
    1090                1095                1100

Gly Val Arg Leu Val Pro Asp Leu Glu Lys Leu Glu Lys Val Asp Gln
1105                1110                1115                1120

Phe Lys Lys Val Leu Phe Ser Leu Gly Gly Ser Phe Leu Tyr Tyr Ala
                1125                1130                1135

Asp Arg Phe Lys Leu Tyr Ser Ala Phe Cys Ala Ile His Thr Lys Val
            1140                1145                1150

Pro Lys Val Leu Val Lys Ala Lys Thr Asp Thr Ala Phe Lys Ala Phe
        1155                1160                1165

Leu Asp Ala Gln Asn Pro Lys Gln Gln His Ser Ser Thr Leu Glu Ser
    1170                1175                1180

Tyr Leu Ile Lys Pro Ile Gln Arg Ile Leu Lys Tyr Pro Leu Leu Leu
1185                1190                1195                1200

Arg Glu Leu Phe Ala Leu Thr Asp Ala Glu Ser Glu Glu His Tyr His
                1205                1210                1215
```

```
Leu Asp Val Ala Ile Lys Thr Met Asn Lys Val Ala Ser His Ile Asn
        1220                1225                1230

Glu Met Gln Lys Ile His Glu Glu Phe Gly Ala Val Phe Asp Gln Leu
        1235                1240                1245

Ile Ala Glu Gln Thr Gly Glu Lys Lys Glu Val Ala Asp Leu Ser Met
    1250                1255                1260

Gly Asp Leu Leu His Thr Thr Val Ile Trp Leu Asn Pro Pro Ala
1265                1270                1275                1280

Ser Leu Gly Lys Trp Lys Lys Glu Pro Glu Leu Ala Ala Phe Val Phe
            1285                1290                1295

Lys Thr Ala Val Val Leu Val Tyr Lys Asp Gly Ser Lys Gln Lys Lys
        1300                1305                1310

Lys Leu Val Gly Ser His Arg Leu Ser Ile Tyr Glu Asp Trp Asp Pro
        1315                1320                1325

Phe Arg Phe Arg His Met Ile Pro Thr Glu Ala Leu Gln Val Arg Ala
    1330                1335                1340

Leu Ala Ser Ala Asp Ala Glu Ala Asn Ala Val Cys Glu Ile Val His
1345                1350                1355                1360

Val Lys Ser Glu Ser Glu Gly Arg Pro Glu Arg Val Phe His Leu Cys
        1365                1370                1375

Cys Ser Ser Pro Glu Ser Arg Lys Asp Phe Leu Lys Ala Val His Ser
        1380                1385                1390

Ile Leu Arg Asp Lys His Arg Arg Gln Leu Leu Lys Thr Glu Ser Leu
    1395                1400                1405

Pro Ser Ser Gln Gln Tyr Val Pro Phe Gly Gly Lys Arg Leu Cys Ala
    1410                1415                1420

Leu Lys Gly Ala Arg Pro Ala Met Ser Arg Ala Val Ser Ala Pro Ser
1425                1430                1435                1440

Lys Ser Leu Gly Arg Arg Arg Arg Leu Ala Arg Asn Arg Phe Thr
        1445                1450                1455

Ile Asp Ser Asp Ala Val Ser Ala Ser Ser Pro Glu Lys Glu Ser Gln
    1460                1465                1470

Gln Pro Pro Gly Gly Gly Asp Thr Asp Arg Trp Val Glu Glu Gln Phe
    1475                1480                1485

Asp Leu Ala Gln Tyr Glu Glu Gln Asp Asp Ile Lys Glu Thr Asp Ile
    1490                1495                1500

Leu Ser Asp Asp Asp Glu Phe Cys Glu Ser Val Lys Gly Ala Ser Val
1505                1510                1515                1520

Asp Arg Asp Leu Gln Glu Arg Leu Gln Ala Thr Ser Ile Ser Gln Arg
            1525                1530                1535

Glu Arg Gly Arg Lys Thr Leu Asp Ser His Ala Ser Arg Met Ala Gln
        1540                1545                1550

Leu Lys Lys Gln Ala Ala Leu Ser Gly Ile Asn Gly Gly Leu Glu Ser
        1555                1560                1565

Ala Ser Glu Glu Val Ile Trp Val Arg Arg Glu Asp Phe Ala Pro Ser
    1570                1575                1580

Arg Lys Leu Asn Thr Glu Ile
1585                1590

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
```

HA-tag sequence

<400> SEQUENCE: 7

Tyr Pro Tyr Asp Val Pro Asp Tyr Ala
 1               5

<210> SEQ ID NO 8
<211> LENGTH: 80
<212> TYPE: PRT
<213> ORGANISM: Mus musculus

<400> SEQUENCE: 8

Glu Arg His Gly Val Ala Phe Tyr Asn Phe Gly Gly Ser Glu Ala Gln
 1               5                  10                  15

His Leu Thr Leu Gln Ile Gly Asp Val Val Arg Ile Gln Glu Thr Gly
            20                  25                  30

Gly Asp Trp Tyr Arg Gly Tyr Leu Ile Lys His Lys Leu Ser Gln Gly
        35                  40                  45

Ile Phe Pro Thr Ser Phe Ile His Leu Lys Glu Val Thr Val Glu Lys
    50                  55                  60

Arg Arg Asn Ile Glu Asn Ile Ile Pro Ala Glu Ile Pro Leu Ala Gln
65                  70                  75                  80